(12) United States Patent
Mellmann et al.

(10) Patent No.: US 10,820,907 B2
(45) Date of Patent: Nov. 3, 2020

(54) OCCLUDER

(71) Applicant: CARAG AG, Baar (CH)

(72) Inventors: Andreas Mellmann, Baar (CH); Jérôme Bernhard, Zürich (CH)

(73) Assignee: Carag AG, Baar (CH)

( * ) Notice: Subject to any disclaimer, the term of this patent is extended or adjusted under 35 U.S.C. 154(b) by 528 days.

(21) Appl. No.: 15/510,695

(22) PCT Filed: Sep. 11, 2015

(86) PCT No.: PCT/EP2015/070797
§ 371 (c)(1),
(2) Date: Mar. 12, 2017

(87) PCT Pub. No.: WO2016/038174
PCT Pub. Date: Mar. 17, 2016

(65) Prior Publication Data
US 2017/0258475 A1    Sep. 14, 2017

(30) Foreign Application Priority Data

Sep. 12, 2014   (EP) ..................................... 14184603

(51) Int. Cl.
*A61B 17/12* (2006.01)
*A61B 17/00* (2006.01)

(52) U.S. Cl.
CPC .... *A61B 17/12122* (2013.01); *A61B 17/1215* (2013.01); *A61B 17/12145* (2013.01);
(Continued)

(58) Field of Classification Search
CPC ........ A61B 17/12027; A61B 17/12031; A61B 17/12036; A61B 17/1204;
(Continued)

(56) References Cited

U.S. PATENT DOCUMENTS 6,488,706 B1 * 12/2002 Solymar ............ A61B 17/0057
                                                       623/3.1
8,801,746 B1    8/2014 Kreidler et al.
(Continued)

FOREIGN PATENT DOCUMENTS

EP         2 074 953 A1    7/2009
WO     2002/102280 A1    12/2002
(Continued)

OTHER PUBLICATIONS

International Search Report for PCT/EP2015/070797 dated Sep. 3, 2016.

*Primary Examiner* — Martin T Ton
(74) *Attorney, Agent, or Firm* — McDonnell Boehnen Hulbert & Berghoff LLP

(57) ABSTRACT

An occluder for occluding a passage in a body, especially in a left atrial appendage (LAA), comprises elongate members having a first end and a second end, the ends being held in or attached to holders, wherein the elongate members extend independently from each other between the holders and wherein the elongate members are collectively enveloped by at least one jacket. The jacket restricts a bending motion of the elongate members when their first ends are approximated to their second ends by moving the two holders relatively to each other. The occluder uses an expanding structure which can be easily handled whereby the movement of the elongate members is restricted by at the jackets which envelop the elongate members. At least the elongate members can be made of bioresorbable material.

17 Claims, 19 Drawing Sheets

(52) U.S. Cl.
CPC ............... *A61B 2017/00526* (2013.01); *A61B 2017/00867* (2013.01)

(58) Field of Classification Search
CPC ........ A61B 17/12045; A61B 17/12099; A61B 17/12122; A61B 17/12145; A61B 2017/0057; A61B 2017/00575; A61B 2017/00592; A61B 2017/00597; A61B 2017/00606

See application file for complete search history.

(56) References Cited

U.S. PATENT DOCUMENTS

| | | |
|---|---|---|
| 8,814,947 B2 | 8/2014 | Callaghan |
| 2002/0156499 A1 | 10/2002 | Konya et al. |
| 2006/0111770 A1* | 5/2006 | Pavcnik ........... A61B 17/12022 623/1.13 |
| 2006/0247680 A1 | 11/2006 | Amplatz et al. |
| 2008/0077180 A1 | 3/2008 | Kladakis et al. |
| 2008/0249562 A1* | 10/2008 | Cahill ................ A61B 17/0057 606/215 |
| 2010/0324538 A1 | 12/2010 | Van Orden |
| 2011/0054515 A1 | 3/2011 | Bridgeman et al. |
| 2012/0065667 A1 | 3/2012 | Javois et al. |
| 2012/0172927 A1 | 7/2012 | Campbell et al. |
| 2013/0131717 A1 | 5/2013 | Glimsdale |
| 2013/0138138 A1 | 5/2013 | Clark et al. |
| 2013/0218193 A1 | 8/2013 | Erzberger et al. |
| 2014/0018841 A1* | 1/2014 | Peiffer ............. A61B 17/12122 606/200 |
| 2014/0058371 A1 | 2/2014 | Krishnan |
| 2014/0135817 A1 | 5/2014 | Tischler et al. |
| 2014/0142612 A1 | 5/2014 | Li et al. |
| 2014/0155932 A1* | 6/2014 | Weishaupt ......... A61B 17/0057 606/200 |
| 2014/0207169 A1 | 7/2014 | Miles et al. |
| 2014/0214077 A1 | 7/2014 | Glimsdale |

FOREIGN PATENT DOCUMENTS

| | | |
|---|---|---|
| WO | 2004082532 A1 | 9/2004 |
| WO | 2005/074813 A1 | 8/2005 |
| WO | 2008/036384 A2 | 3/2008 |
| WO | 2010/151509 A1 | 12/2010 |
| WO | 2012/156415 A1 | 11/2012 |

* cited by examiner

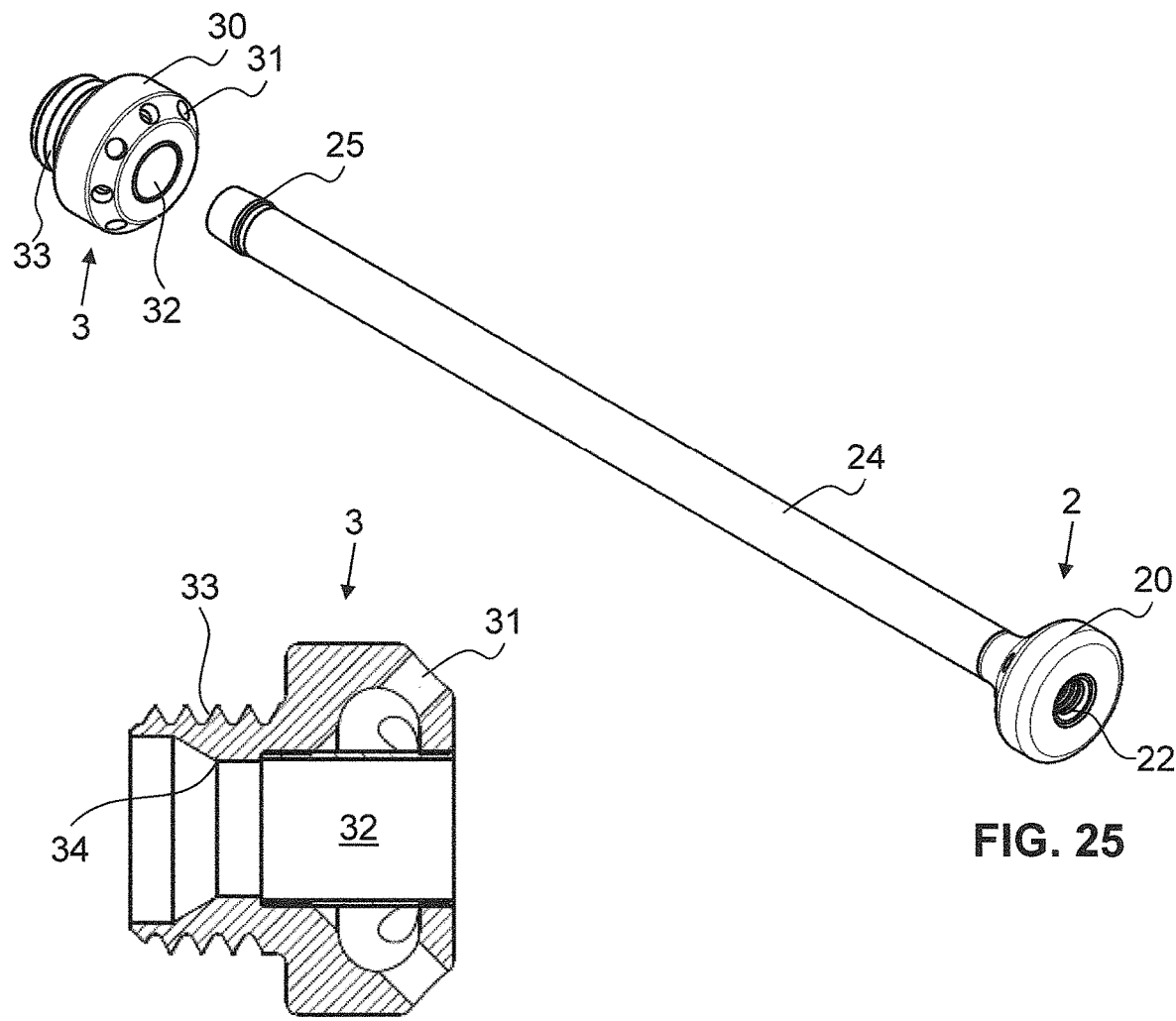
FIG. 25
FIG. 26
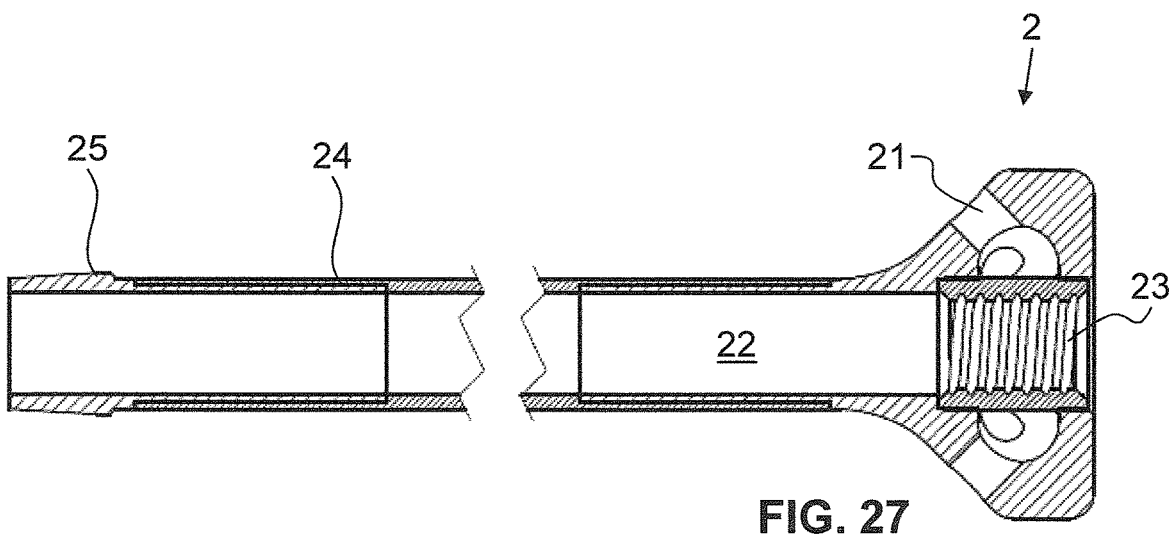
FIG. 27

OCCLUDER

CROSS REFERENCE TO RELATED APPLICATIONS

The present application is a U.S. National Phase Application pursuant to 35 U.S.C. § 371 of International Application No. PCT/EP2015/070797 filed Sep. 11, 2015, which claims priority to European Patent Application No. 14184603.0 filed Sep. 12, 2014. The entire disclosure contents of these applications are herewith incorporated by reference into the present application.

TECHNICAL FIELD

The present invention relates to an occluder for occluding a passage in a body, especially to a left atrial appendage occluder, and a method to produce such an occluder.

PRIOR ART

A variety of devices and techniques have been developed to occlude a vessel or an opening in an organ, such as the heart, of a patient.

U.S. Pat. No. 6,488,706 discloses a well-working implant for occluding a passage in a circulatory system. This implant has its particular application as a cardiological implant by means of which it is possible, for example, to close an aperture through the atrial septum or the ventricle septum of a heart. It is arranged to be introduced with a catheter and deployed or built up at a desired location in the body. This occluder comprises a plurality of thin wire-like elongate members which form a fixation structure and a single occluding body, namely a disk-like membrane, which is expanded by the fixation structure in the body passage. The fixation structure is locked in its expanded state by a locking unit. This locking unit comprises two locking elements which are brought together when the occluding body is expanded.

WO 2005/074813 discloses an occluder working with the same principle but comprising two occluding bodies which are expanded by the fixation structures. This occluder securely closes both sides of the passage. In WO 2012/156415 this occluder further comprises a jacket which envelops at least a part or a portion of the expanding unit so that no parts of the occluder can wander within the human or animal body. This jacket also enhances the growth of the body tissue over the occluder.

These above mentioned occluders form with their twisting elongate members the fixation structure. This has the advantage that the occluders can be opened and closed at a pace given by the user. Therefore the location within the body passage can be changed until the fixation structure is locked in its expanded form by the locking unit.

WO 2010/151509 discloses an occluder for repair of cardiac and vascular defects or tissue openings. The occluder comprises an expandable frame consisting of elastic wires and a film encapsulating the expandable wire frame to enhance cellular growth.

The closure of the left atrial appendage (LAA) however is a special task. The LAA is a small projection from the upper anterior portion of the left atrium. Blood pooling in the LAA may arise spontaneously or as a result of atrial fibrulation. When blood pools in the LAA, blood clots can be formed. The migration of clots from the LAA to the other parts of the body can cause loss of circulation to the affected organ or, when the clots migrate to the brain, it can even cause strokes. Since LAA is a complex and heterogeneous structure with a rather elliptical ostium, it challenges the sizing and shaping of the occluders. The occluders have to be sized and shaped individually for each patient. Since the tissue of the cardiac structure LAA is very thin and fragile, the risk of damaging the tissue when placing the occluder is permanent as well.

In addition, some occluders may be undesirably expelled from the LAA due to forces generated by the heart beat or by atrial fibrulation. Usually quite big and stable occluders have to be used, which makes delivering of the implant to the LAA more difficult. In addition, these occluders have to remain within the LAA passage, even when they are already overgrown.

Occluders for LAA are for example disclosed in US 2013/0138138, US 2011/0054515, US 2014/0135817, EP 2 9074 953, US 2014/0142612, US 2013/0131717, US 2014/0214077, US 2006/0247680, US 2012/0065667, US 2014/0058371, U.S. Pat. No. 8,801,746, US 2014/0207169, WO 2004/0-882532 and US 2012/0172927.

Usually, they use metal self-expandable meshes or frameworks. The meshes or frameworks are spring-like or have shape-memory. Some use caps coupled to self-expanding frames. Some of them have hooks or anchors to fix the occluder within the passage.

US 2013/0218193 discloses an implant for LAA which includes a cap that overlies the opening of the LAA connected to a bulb in the LAA. Discontinuous segmented sails attached to the cap promote tissue growth over the device. This device can be repositioned and redeployed during implantation, wherein the single parts of this occluder are not really guided during deployment.

SUMMARY OF THE INVENTION

It is therefore an object of the invention to provide an improved occluder, which is especially suitable for the closure of the left atrial appendage (LAA), and a method to produce such an occluder.

The inventive occluder for occluding a passage in a body comprises elongate members, each elongate member having a length with a first end and a second end, the first end being held in or attached to a first holder and the second end being held in or attached to a second holder. The elongate members extend independently from each other between the first and the second holder and they are collectively enveloped at least over a part of their length by at least one jacket. At least one of the at least one jackets restricts a bending motion of the elongate members when their first ends are approximated to their second ends by moving the two holders relatively to each other.

The elongate members form a framework of the occluder, i.e. an expanding and fixation unit or structure, which expands the occluder from a compressed state into an expanded final state and which holds the expanded occluder in this state. The expanded final state is achieved by approximating the two holders to each other. However, the two holders have not to be brought into contact with each other. In preferred embodiments, they remain at a distance to each other or they are locked with each other such that they can still perform a movement relative to each other along the longitudinal axis, at least in one direction. In other embodiments they are fixedly locked to each other and no relative movement is possible any more. However, in preferred variants of this embodiment, a middle part of the holder system is made of a flexible material and remains flexible.

The inventive occluder uses the well-working expanding system of the occluders disclosed in U.S. Pat. No. 6,488,706, US 2003/0149463, WO 2005/074813 and WO 2012/156415. The movement of the elongate members held in two holders can be controlled in any stage of the procedure. The two holders can be moved independently from each other and therefore, the occluder can be recompressed and once again expanded as often as needed. Since a guide wire can be used, the occluder can be exactly introduced at the place to be occluded in a quite easy and efficient way.

By restricting the bending motion, the jacket or cover forces the framework of the occluder, i.e. the elongate members, into its shape, when it is expanded into its final form. The invention therefore allows various shapes of occluders, particularly suited for transcatheter closure of let atrial appendage (LAA). Occluders having individually chosen shapes and sizes can be made from the same basic material. By choosing the size and shape of the jacket and by attaching the elongate membrane to this jacket, individually sized and shaped occluders can be created. Therefore, the inventive occluder can be made to match all sizes and shapes of LAA openings. In preferred embodiments, the at least one jacket restricting the bending motion of the elongate members has a bell-like shape. However, other shapes can be used as well.

Preferably, the elongate members are at least in the expanded final state of the occluder completely covered by jackets and, if applicable, by membranes. This enables to use thin elongate members without the risk that they break and wander within the patient's body. This allows for a broader variety of materials to be used for producing the occluder. This even also allows for occluder with bioresorbable or remodelable framework and bioresorbable or remodelable cover, even when used for LAA. The whole occluder can be made bioresorbable or biodegradable or bioabsorbable or remodelable.

LAA closure devices are endothelialized shortly after implantation. Once such devices are covered by body tissue and ingrown, the entire occluder, or at least its framework, i.e. the elongate members, becomes obsolete. The tissue of the cardiac structure LAA is very thin and fragile. A permanent, i.e. metallic, device bears the life long deadly risk of erosion, perforation and damaging the surrounding anatomical structures. An occluder with bioresorbable or remodelable framework that goes away after endothelialization is a benefit for the patient since erosion or perforation is very unlikely to happen. In preferred embodiments, the cover can bioresorb or can be remodeled as well, i.e. the jackets and the membranes. In some embodiment, the other parts of the occluder are bioresorbable or remodelable as well.

In preferred embodiments, at least a portion of the length of the elongate members are sewed to the at least one jacket. No other items are needed for attaching the elongate members to the jacket. In other embodiments, the at least one jacket comprises pockets which extend along the length of the jacket and which comprise open ends on both facial sides. Each elongate member is arranged within such a pocket, thereby penetrating the pocket on both open ends. Each elongate member has preferably its own pocket. Depending on the kind of jacket, the elongate member is held movable within the pocket relative to the pocket and in direction of the length of the elongate member. The pockets can be additionally attached to the jacket, for example sewed, welded or clamped. The pockets can also be made by folding the material of the jacket and by fixing them with known means, such as sewing, welding or clamping.

Preferably, all of the elongate members are sewed to the at least one jacket. Like this, the desired shape of the occluder in its expanded state can easily be achieved. There can be different types of jackets. Not all jackets have to restrict the bending motion of the elongate members. The jackets restricting the motion can be called restricting jackets, the jackets allowing the bending motion can be called covering jackets. Parts of the at least one membrane, if present, can also form a jacket or cover.

In preferred embodiments, the elongate members are restricted in their bending motion by at least a portion of their length. By choosing the portion to be restricted, the shape of the occluder in its final expanded state can be chosen.

Fixation of an LAA occluder can not be achieved by clamping on an anatomical structure like it is the case with a septal occluder. The LAA is an unneeded cardiac structure without blood flow once closed. As a consequence, an LAA occluder does not need to be flat/disc like on both sides as it is favorable for septal occluders. Only the side facing the left atrium, i.e. the proximal portion of the occluder, is preferably flat. The side lying within the LAA, i.e. the distal portion, can fill out the cavity. By doing so, the occluder is fixed within the LAA, preferably without the need for additional retention or fixation elements.

In a preferred embodiment, the occluder comprises at least a first jacket and a second jacket, wherein the portion of the length of the elongate members restricted in its bending motion is surrounded by the second jacket and wherein a portion of the length of the elongate members arranged in the first jacket is not restricted in its bending motion or less restricted than the portion of the elongate members arranged in the second jacket.

In a preferred embodiment, the occluder further comprises an occluding membrane penetrated by the elongate members, wherein the occluding membrane is deployable by a twisting motion of the elongate members when the first holder and the second holder are moved relatively to each other. The membrane preferably extends in the expanded final state at least approximately perpendicular to the longitudinal axis of the occluder. The membrane has preferably a thin disk-shaped form. However, it does not have to be round but can also have other cross-sections as well, such as oval.

The jackets can be attached to each other or to the membrane by any suitable means. Preferably they are sewed to each other. However, they can also be welded or clamped or otherwise attached to each other. The jackets can also be made in one single piece, thereby forming a unitary and single-piece jacket or cover.

In a preferred embodiment the occluding membrane is fixed to the first jacket and the second jacket is fixed to the occluding membrane, wherein the bending motion of a portion of the elongate members enveloped by the second jacket is restricted. In another embodiment, the membrane and the at least one jacket is made of one in one single piece.

In a preferred embodiment the occluding membrane is fixed to the first jacket and the second jacket is fixed to the occluding membrane, wherein the portions of the elongate members arranged within the first jacket are fixed to the first jacket allowing movement of the elongate members relative to the first jacket and wherein the portions of the elongate members arranged within the second jacket are fixed to the second jacket allowing less or no movement relative to the second jacket, so that the bending motion of these portions of the elongate members is restricted by the second jacket.

Preferably, the first jacket allows a twisting motion of the portions of the elongate members enveloped by the first jacket.

In a preferred embodiment, the occluder comprises a third jacket wherein the third jacket is fixed to the second jacket on a side opposite to the occluding membrane and wherein the third jacket allows more motion of the portion of the elongate members enveloped by this third jacket.

A preferred occluder with at least some of the above mentioned features has a distal portion that adapts to the LAA anatomy and is thereby fixed within the LAA cavity. It has a proximal portion that configures flat and thereby seals the LAA against the left atrium.

In another preferred embodiment, the occluder comprises a first jacket, a second jacket fixed to the first jacket and a third jacket fixed to the second jacket, the first, second and third jacket forming a common bag and the elongate members being fixed along their length to the first, second and third jacket, and wherein the second jacket restricts the bending movement of the elongate members more than the first and third jacket. Preferably, no occluding membrane is present. Preferably the elongate members are twisting with their enveloping first, second and third jackets into a cup-shaped form when the two holders are brought together.

Preferably, hooks or other retaining means are arranged on the outside of one of the at least one jacket.

Preferably, the at least one jacket is made of polyester fabric, bioresorbable fabric or a collagen patch. The same applies for the membrane. The elongate members are preferably made of Nitinol or PLA (polylactide), PGA (polygycol acid) or blends thereof. Most preferably, they are made of PLGA (poly(lactic-co-glycolic acid)). If sutures or threads are used to fix the elongate members to the at least one jacket, they are preferably made of PDS (polydioxanone) or prolene. The holders as well are preferably bioresorbable and preferably made of PLA (polylactide), PGA (polygycol acid) or blends thereof or of PEEK. They are in some embodiment made of PLGA (poly(lactic-co-glycolic acid)). The materials mentioned in U.S. Pat. No. 6,488,706, US 2003/0149463, WO 2005/074813 and WO 2012/156415 can also be used for the elements mentioned above.

In a preferred embodiment the first holder comprises a through hole with a first retaining element and the second holder comprises a stem with a second retaining element, wherein the first and the second retaining element are brought into engagement with each other in an expanded final state of the occluder. This holder system can also be used in other occluders as well, such as the ones known in the state of the art. This holder system is therefore claimed herein as a separate invention as well.

In a preferred embodiment, the first and the second holder are able to move along the stem relative to each other in the expanded final state wherein the first and the second retaining element together form an abutment of this movement.

The inventive method to produce an occluder comprises the steps of
  attaching elongate members of the occluder to at least one jackets, wherein each elongate member is attached separately,
  bringing the occluder with the attached elongate members into an expanded shape by approximating the two holders connected with the elongate members to each other,
  holding the occluder in this expanded shape and
  heating the occluder to mechanically and thermally preforming the occluder.

This expanded state is preferably the preferred final expanded state or a state similar to this final state.

After the occluder has or is cooled down again or shortly before it is used, the occluder can be compressed to be introduced with the sheath catheter into the patient's body. When the occluder is deployed and expanded, it will remain in its expanded final state, even without additional locking or fixation means, since it was already pre-shaped into an expanded form.

Another inventive occluder, which is preferably also thermally and mechanically preformed according to the method described above, comprises elongate members, each elongate member having a length with a first end and a second end, the first end being held in or attached to a first holder and the second end being held in or attached to a second holder, wherein the elongate members extend independently from each other between the first and the second holder, wherein the elongate members are collectively enveloped at least over a part of their length by at least one jacket. The occluder further comprises a first occluding membrane and a second occluding membrane, the first and second occluding membranes being penetrated by the elongate members, wherein the first and second occluding membranes are deployable by a twisting motion of the elongate members when the first holder and the second holder are moved relatively to each other. The first and second occluding membranes are fixed to the at least one jacket. One of the at least one jacket is a middle jacket arranged between the first and the second occluding membrane. The elongate members extend within this middle jacket none-attached to the middle jacket.

This occluder as well is especially suited for use in LAA. It has also the advantage that its shape and size can be individually chosen by still using the advantages of the guided expansion and recompression of the occluder because of the expanding structure.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 25 shows a perspective view of a pair of holders in another embodiment;

FIG. 26 shows a proximal holder according to FIG. 25 in a longitudinal sectional view;

FIG. 27 shows a distal holder according to FIG. 25 in a longitudinal sectional view;

Figures with numbering "a" and "b" show the same items, the figures named "a" being photos and figures named "b" being drawings. In the following description reference is made to the figure only without "a" and "b", thereby meaning both figures.

DESCRIPTION OF PREFERRED EMBODIMENTS

Figure 1:
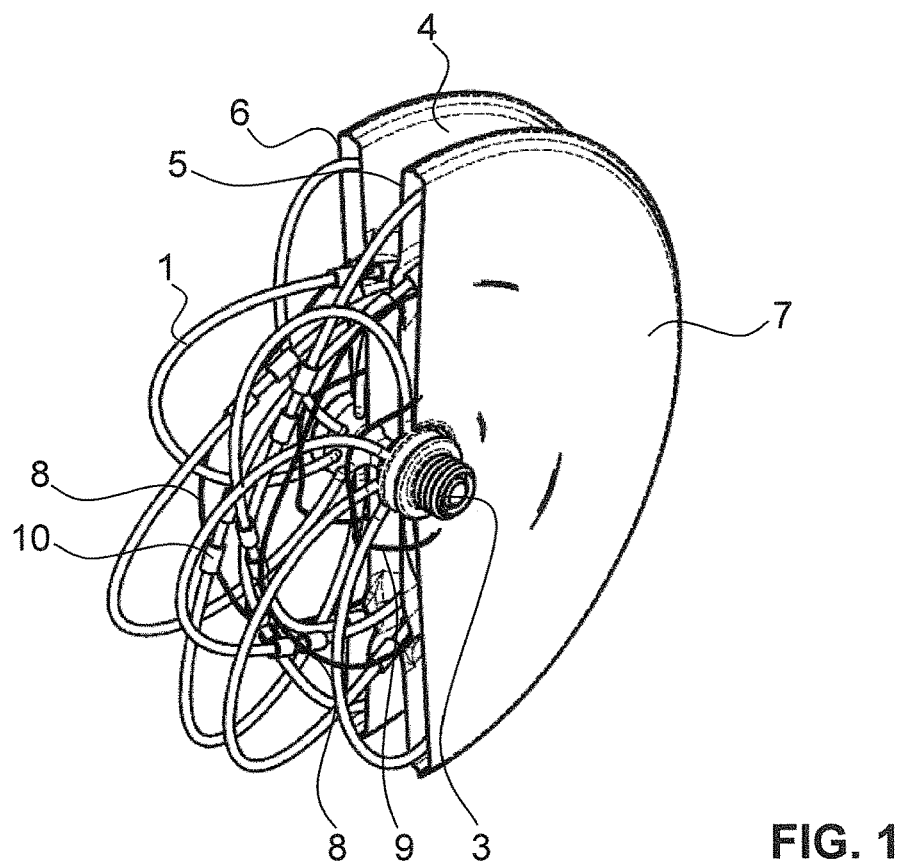
FIG. 1 shows a partial sectional view of an occluder according to the state of the art in an expanded state.

The occluder according to the preferred embodiments is based on the implants disclosed in WO 2005/074813, U.S. Pat. No. 6,488,706, US 2003/0149463 and especially as disclosed in WO 2012/156415. The main principle of the occluder mechanism according to this state of the art is shown in FIGS. 1 and 2.

Figure 2:
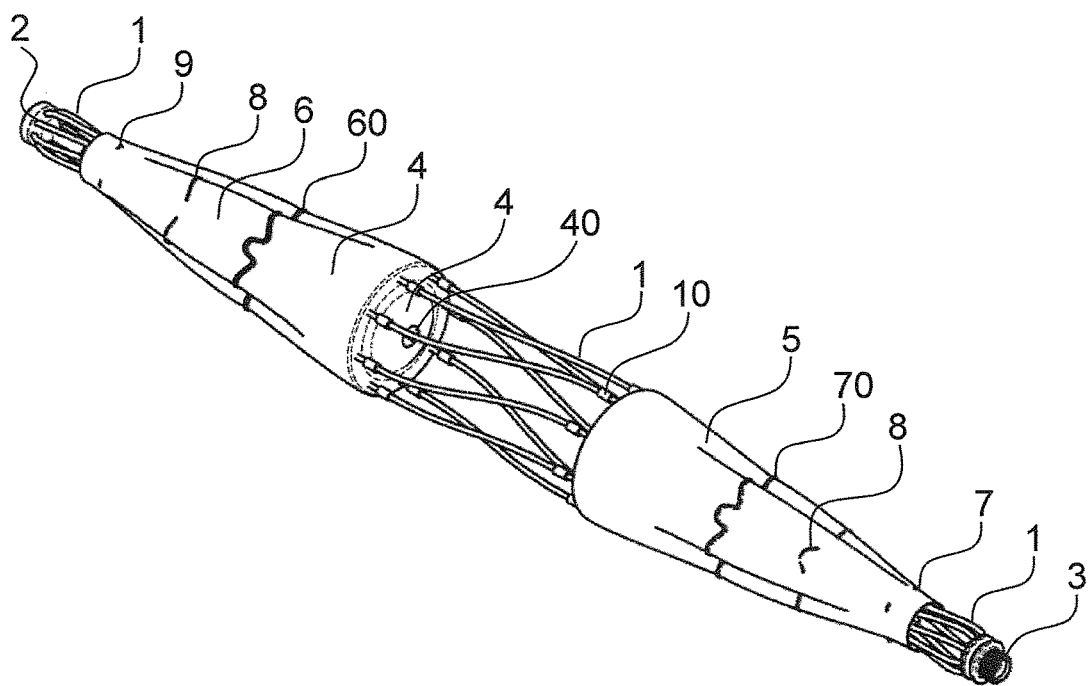
FIG. 2 shows the occluder according to FIG. 1 in an almost completely compressed state.

As shown in FIG. 2, the occluder is compressible for insertion through a delivery mechanism, such as an introduction sheath introduced in a body vein or artery or body vessel, and is deployable or expandable for occluding the passage when arrived at the position of the intended closing spot.

The occluder comprises at least one occluding body, here two occluding bodies or membranes 4, 5, an expanding unit consisting of a multiple of thin elongate members 1, a first holder 2 and a second holder 3.

The elongate members 1 are flexible and can be bent, but preferably they have no elasticity in direction of their longitudinal axis. They are preferably stiff and inextensible. Each elongate member 1 is thin and made as a unitary single piece with a first end and a second end. The first end is attached to or held in the first holder 2. The second end is attached to or held in the second holder 3. The elongate members 1 are arranged separate from each other and are not directly connected to each other; i.e. they are preferably separate wires or filaments and not part of a net or otherwise connected.

When the two holders 2, 3 are brought together, the elongate members 1 are compressed longitudinally. In the embodiments according to the state of the art shown in FIGS. 1 and 2, they automatically bend and twist sideways to be formed into two circular or loop shapes, similar to a flower, a propeller or an umbrella. These twisted shapes form fixation structures. These structures lay, when the occluder is implanted, on the surrounding tissue on both sides of the passage to be closed and fix the occluder at this position.

In the embodiments according to the state of the art, the two holders 2, 3 have locking elements which lock the occluder in this expanded shape and therefore lock the fixation structures in their shapes.

The first and second occluding bodies 4, 5 are thin membranes, which are located between the two holders 2, 3. They are preferably round, disk-shape and almost flat. They are made of a flexible material so that they can be folded or compressed when introduced into the introduction sheath. In the extended and deployed state of the occluder, they are extended as well, at least an inner region of the membranes being expanded into a round, disk-shaped form. Preferably, they are usually not tense in this expanded position so that they can abut the surrounding tissue of the passage to be closed. In the figures, the occluding bodies appear to be quite stiff and their compressed and actual flexible shapes are not realistically shown.

The occluding bodies 4, 5 extend in a radially manner from the longitudinal axis of the elongate members 1. Preferably they are arranged concentrically to this axis. Also preferably, both membranes are identical and their distance to their neighboring holder 2, 3 is identical. Each occluding body 4, 5 comprise a central hole 40. These holes 40 as well as corresponding holes in the two holders 2, 3 are penetrated by a guide wire when the occluder is introduced with an introduction sheath into the body passage.

The occluding bodies 4, 5 comprise on their circumference holes which are penetrated by the elongate members 1. The holes are preferably arranged in evenly distances from each other. The elongate members 1 preferably comprise fixation bushes 10 on at least one, preferably on both sides of the membranes 4, 5, which enable the membranes 4, 5 to move for only a short distance along the elongate members 1. Theses bushes 10 can also be used as X-ray markers, especially when the elongate members are invisible for X-ray. The bushes 10 are preferably made of metal, such as platinum-iridium or of a degradable but X-ray-visible material such as a blend of a polymer with BaS.

The occluding bodies 4, 5 divide each of the elongate members 1 in three portions. A first portion lies between the first holder 2 and the first membrane 4. A second portion lies between the two membranes 4, 5 and the third portion lies between the second membrane 5 and the second holder 3. The first and third portions form in the expanded and twisted position the first and second fixation structure. The second portion has in this state a coil-like or stent-like shape. Preferably at least the first and third portions of the elongate members 1 have the same length.

The flower-like fixation structures can be surrounded by protecting jackets 6, 7. When jackets are used, the holes in the membranes 4, 5 for penetration by the elongate members 1 are preferably arranged at a substantial distance to their circumferential edge, giving enough material on the outer circumference of the membranes to connect the jackets 6, 7.

In the embodiments according to the state of the art, the elongate members 1 can move relative to the jackets 6, 7, wherein the jackets 6, 7 are loosely attached to at least some of the elongate members by sutures or threads 8, 9. The jackets 6, 7 are sewed to the first and second membranes 4, 5. The sewing seams have the reference numbers 60 and 70. The elongate members 1 can still twist into their flower-like shape.

FIGS. 3 to 7 show a first embodiment of an inventive occluder especially capable to be used for closing a left atrial appendage (LAA). The expanding structure is the same as described above. It comprises a multiple of thin elongate members 1, wherein each elongate member 1 is attached or held with one end in the first holder 2 and with the other end in the second holder 3. Preferably, the occluder comprises 3 to 10 elongate members 1, most preferably 8 elongate members.

The first holder 2 is a distal holder, the second holder 3 is a proximal holder. Preferably, both holders 2, 3 include markers for X-ray guidance. For example, the first holder 2 includes a Phynox-nut and the second holder 3 includes a PtIr-marker. The elongate members 1 are preferably made of resorbable PLGA filaments.

The occluder further comprises the first membrane 4 and the first cover or jacket 6 as described above, wherein the first membrane 4 and the first jacket 6 are here, contrary to FIGS. 1 and 2, arranged on the proximal side of the occluder. The fixation bushes 10 restricting the movement of the first membrane 4 relative to the elongate members 1 can best be seen in FIG. 3. The elongate members 1 penetrate the first membrane 4, their penetration region forming a circle being co-centric with the central opening 40 of the membrane. The fixation bushes 10 are arranged on the outside of this penetration region, i.e. facing the distal side of the occluder. "Distal" means directed to the patient, "proximal" means directed to the physician.

The first jacket 6 is sewed to the elongate members 1 with at least one first suture or thread 8 and the first jacket 6 is sewed to the first membrane 4. The according first seam has the reference number 60. The stitches made with the at least one first suture or thread 8 are guiding elements only, so that the elongate members 1 can still move relative to the first jacket 6. The stitches of the at least one first suture or thread 8 extend preferably along the whole length of the portion of each elongate member 1 covered by the first jacket 6.

The first membrane 4 and the first jacket 6 are preferably made of woven polyester fabric or of the other materials mentioned before.

According to the invention, there is a second cover or jacket 7 but not a second membrane. The first membrane 4 will therefore be called occluding membrane 4 furtheron.

Figure 3A:
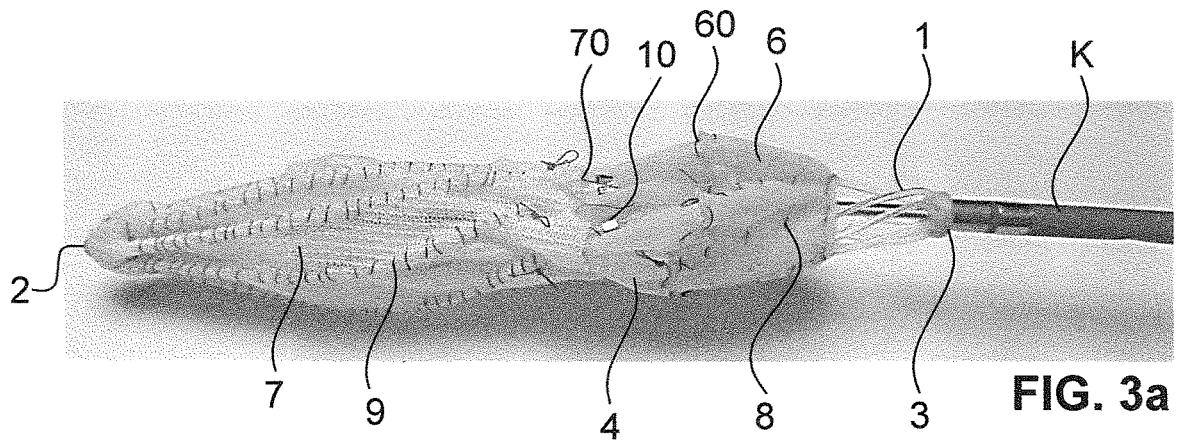
FIGS. 3a and 3b show a perspective view of an occluder according to a first embodiment of the invention in an almost completely compressed state.
Figure 3B:
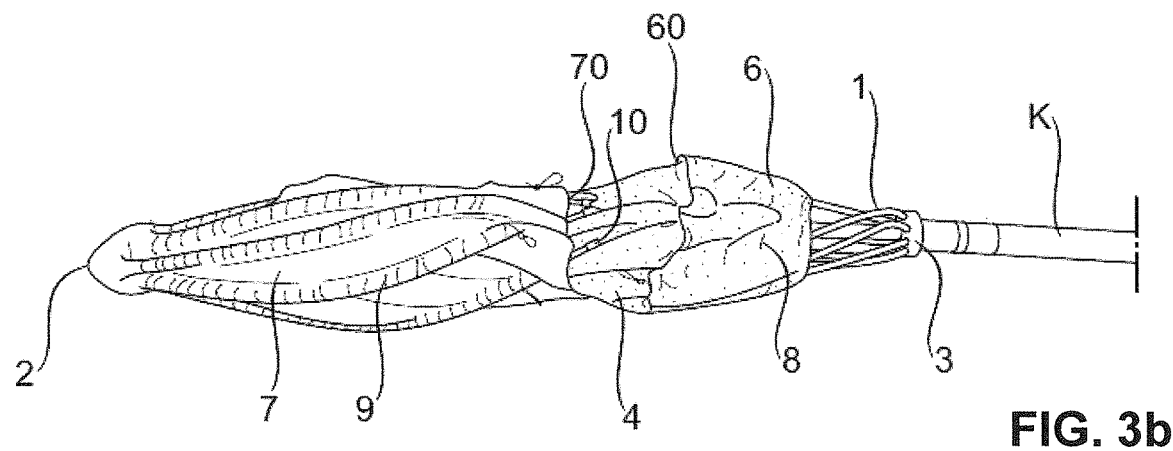

The second jacket 7 is a restricting jacket. It is attached to the occluding membrane 4, preferably at a circle of the occluding membrane 4, the circle being bigger than the circle defined by the penetration points of the elongate members 1. I.e. the second jacket 7 covers the elongate members 1 and the bushes 10 on the distal side of the occluding membrane 4, at least when the occluder is expanded. In FIG. 3, the bushes 10 can still be seen. Instead of bushes alternative fixation elements can be used as well. For example, there can be bushes on the distal or proximal side of the membrane only.

Figure 4A:
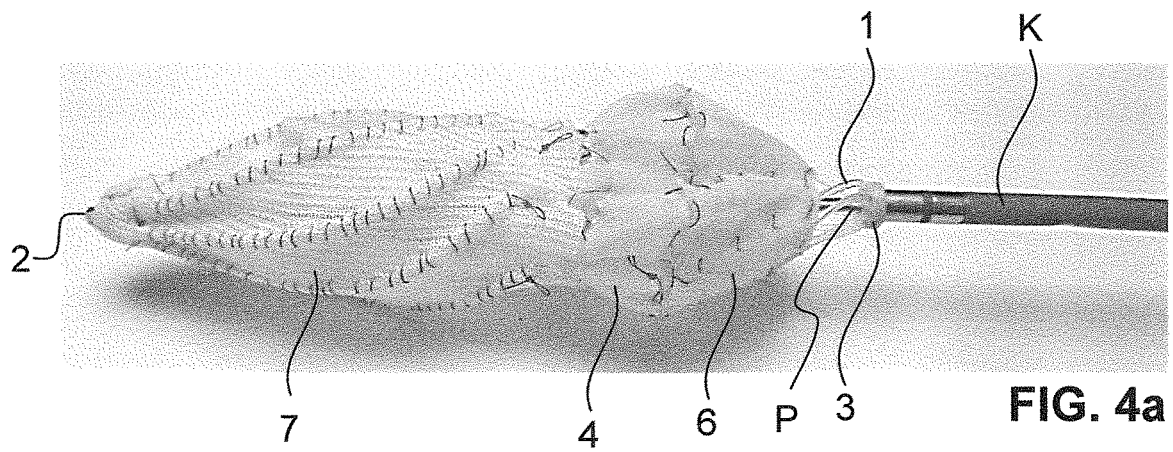
FIGS. 4a and 4b show the occluder according to FIG. 3 in a partly deployed or expanded state.
Figure 5A:
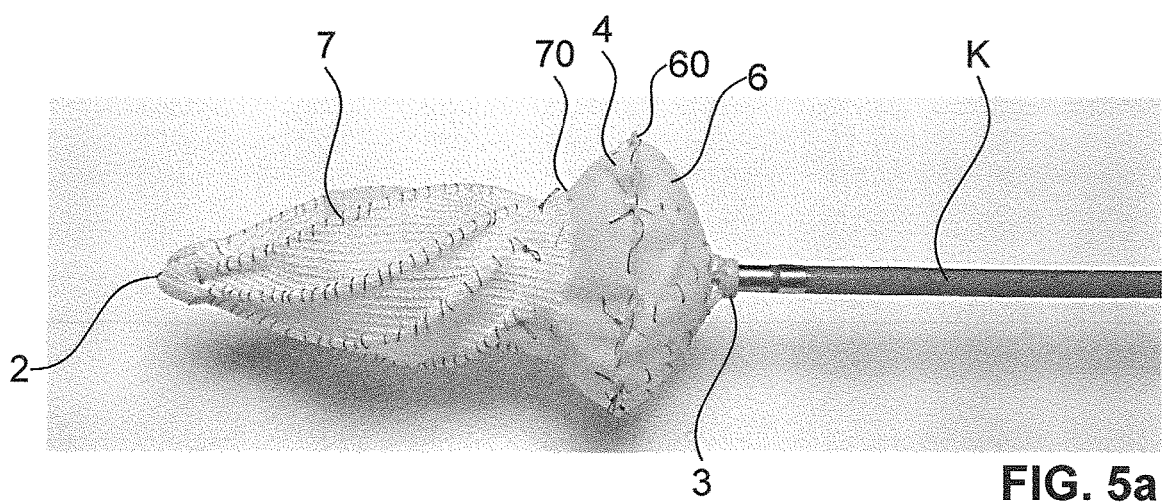
FIGS. 5a and 5b show the occluder according to FIG. 3 in a more deployed or expanded state.
Figure 4B:
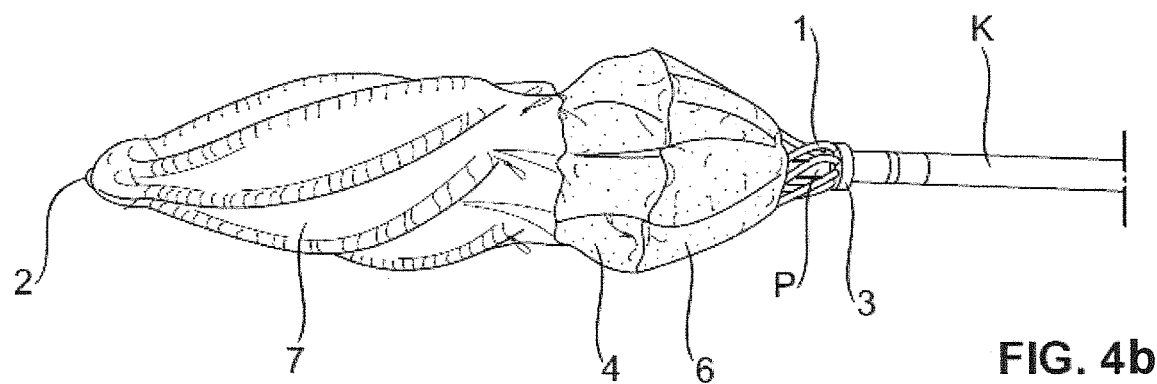
Figure 5B:
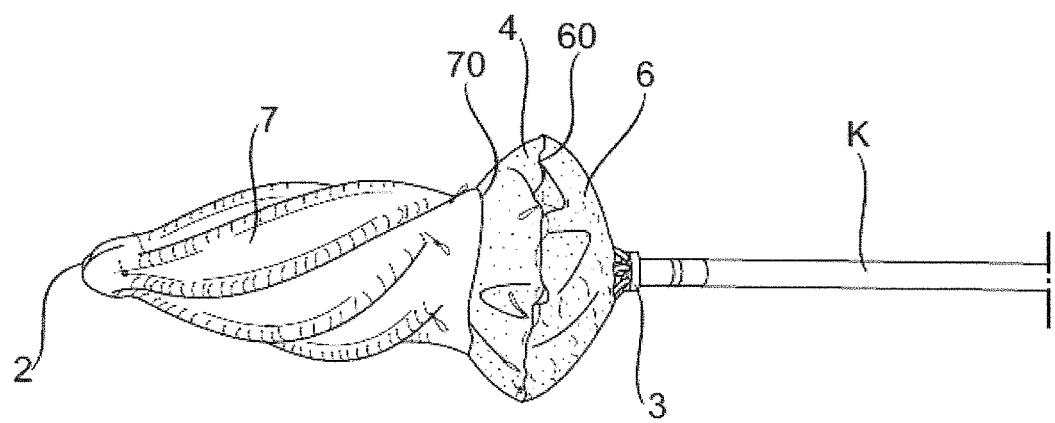

The second jacket 7 is preferably fixed to the occluding membrane 4 with a second seam 70, which can be quite loose. In FIGS. 4 and 5, the at least one thread forming the second seam 70 is more tense and the bushes 10 are now covered by the jacket 7.

The second jacket 7 can be made of the same basic material as the first jacket 6. This is the case in this embodiment. However, the second jacket 7 is made of a knitted material, the first jacket 6 of a woven material. The first jacket 6 is preferably stiffer and/or less elastic than the second jacket 7.

Figure 18:
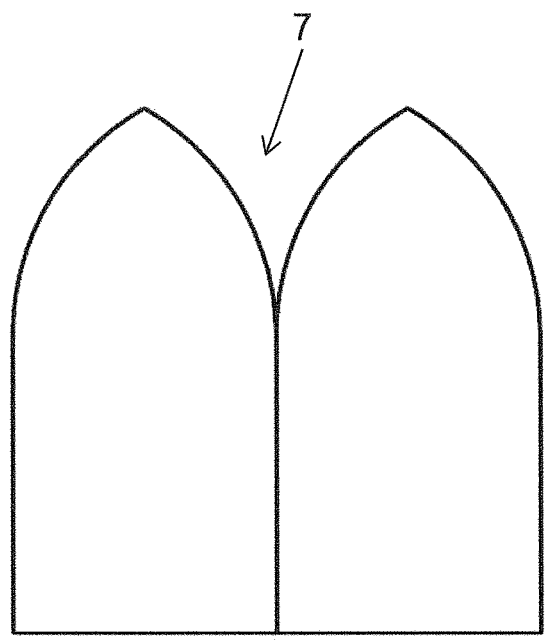
FIG. 18 shows a schematically view of a restricting jacket before it is joined into its final shape.

FIG. 18 shows a basic shape of the second jacket 7, before it is closed into its generally bell-like shape.

As can be seen in the figures, the elongate members 1 are sewed to the second jacket 7 as well. The at least one second suture or thread is marked with the reference number 9. The stitches of this second suture or thread 9 are placed nearer to each other than the stitches of the first thread 8. In addition, they are tenser, so that they are not just guiding elements but are restricting the relative movement of the elongate members 1 relative to the second jacket 7 to a minimum or are even allowing no relative movement at all. Preferably, each elongate member 1 is sewed to the second jacket 7 with a separate second suture or thread 9. Preferably, the portion of each elongate member 1 covered by the second jacket 7 is sewed to the second jacket 7 along its entire length.

Figure 19:
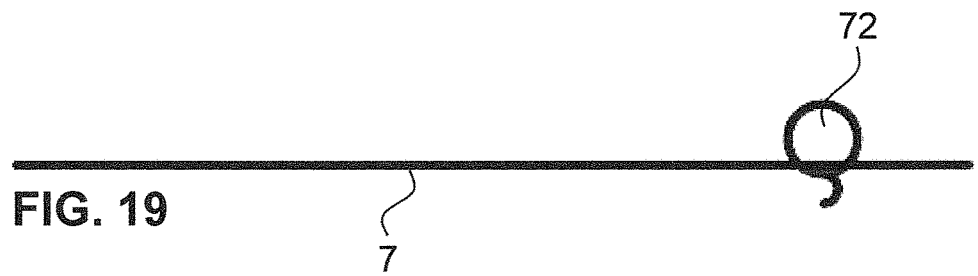
FIG. 19 shows a schematically view of a jacket where the elongate member is sewed to the jacket.
Figure 20:
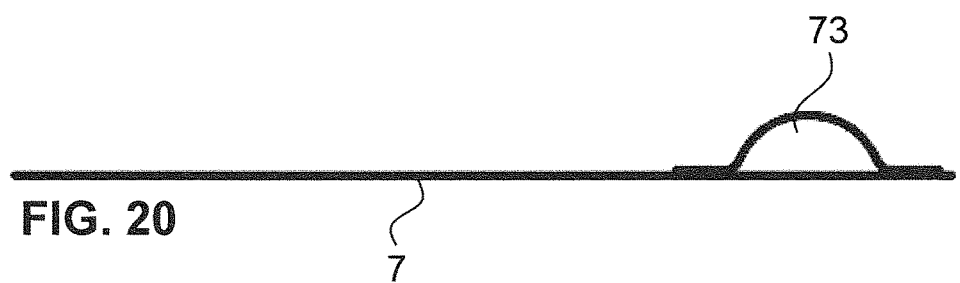
FIG. 20 shows a schematically view of a jacket with a pocket attached to the jacket.
Figure 21:
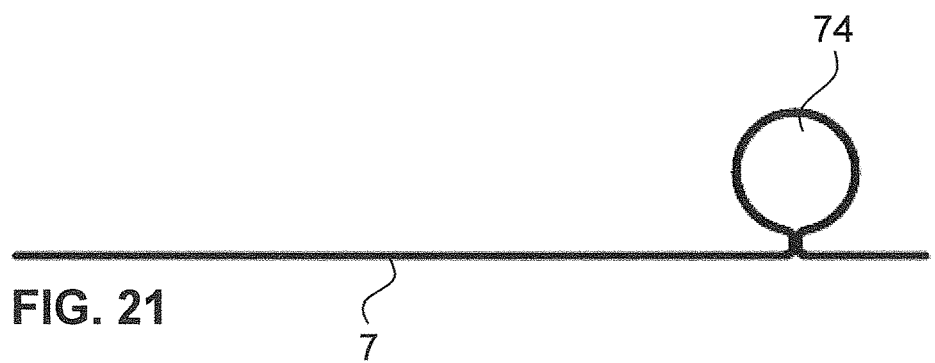
FIG. 21 shows a schematically view of a jacket with a pocket made of the jacket itself.

FIG. 19 shows schematically a loop 72 of seam 9 which is used to attach the elongate member 1 to the second jacket 7. The elongate members 1 can be attached to the jackets 6, 7 by other means as well. For example, the jackets 6, 7 can comprise pockets 73, 74 on their inside, wherein the pockets 73, 74 are open on both ends and the elongate members 1 can be pushed or pulled into the pockets. Preferably only one single elongate member is received in a pocket. FIG. 20 shows a pocket 73 attached to the second jacket 7, for example it is sewed or welded or clamped to it. FIG. 21 shows a pocket 74 formed by the second jacket 7 itself, for example it is sewed or welded into its shape.

FIGS. 3 to 7 show how the occluder can be brought into the expanded state. In FIG. 3, the occluder is almost compressed. It will be even more compressed when introduced into the delivery sheath. Attached to the second holder 3 is a delivery catheter K of the delivery mechanism. Within the catheter K, a control catheter P is movably arranged, which extends to the first holder 2. The control catheter P is attached to the first holder 2, thereby enabling a movement of this first holder 2 independently from the movement of the second holder 3. The control catheter P has a through opening for the guide wire.

Figure 7A:
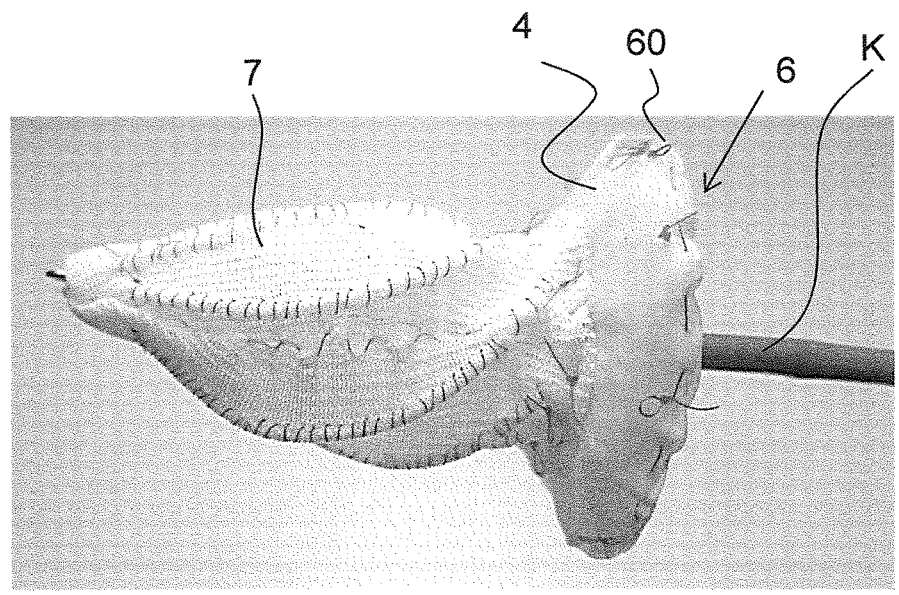
FIGS. 7a and 7b show the occluder according to FIG. 3 in a fully deployed or expanded state from a second side.
Figure 7B:
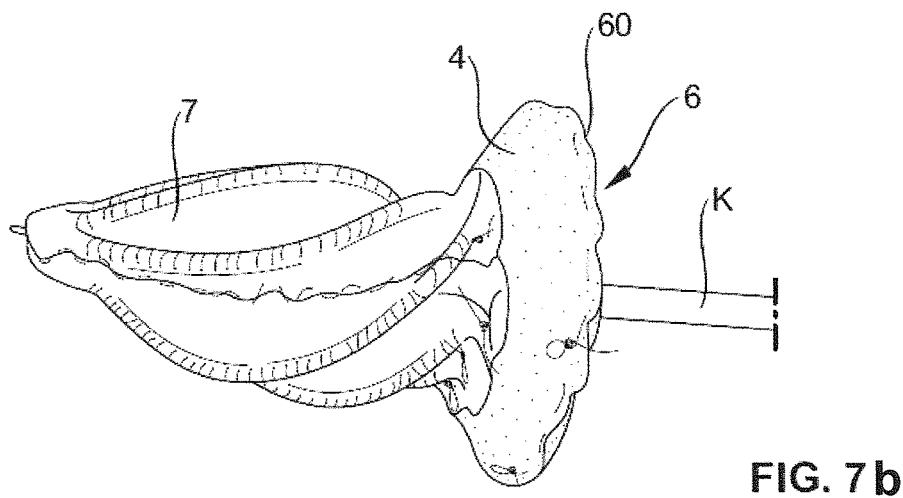

By movement of the catheter K and the control catheter P relative to each other, the first and second holder 2, 3 can be brought nearer to each other. The parts of the elongate members 1 arranged within the bag formed by the occluding membrane 4 and the first jacket 6 bend and twist into the flower shape known from the occluders of the state of the art. The occluding membrane 4 is expanded into a shape similar to a disk, as can be seen in FIG. 7, wherein these parts of the elongate members 1 remain covered by the occluding membrane 4 and the first jacket 6. The bag formed by the first membrane 1 and the first jacket 6 is compressed into an expanded shape.

The parts of the elongate members 1 arranged within and fixed to the second jacket 7 however only slightly change their shape. The movement of the elongate members 1 is mainly restricted by the geometry of the restricting second jacket 7 and by the fixation of the elongate members 1 to this restricting second jacket 7. These parts of the elongate members 1 are especially hindered in their twisting motion and can therefore not take the flower-shaped form as the other parts which are arranged within the bag made of the occluding membrane 4 and the first jacket 6. The second jacket 7 therefore remains elongated and takes the shape similar to a pine cone or a bell.

Figure 6A:
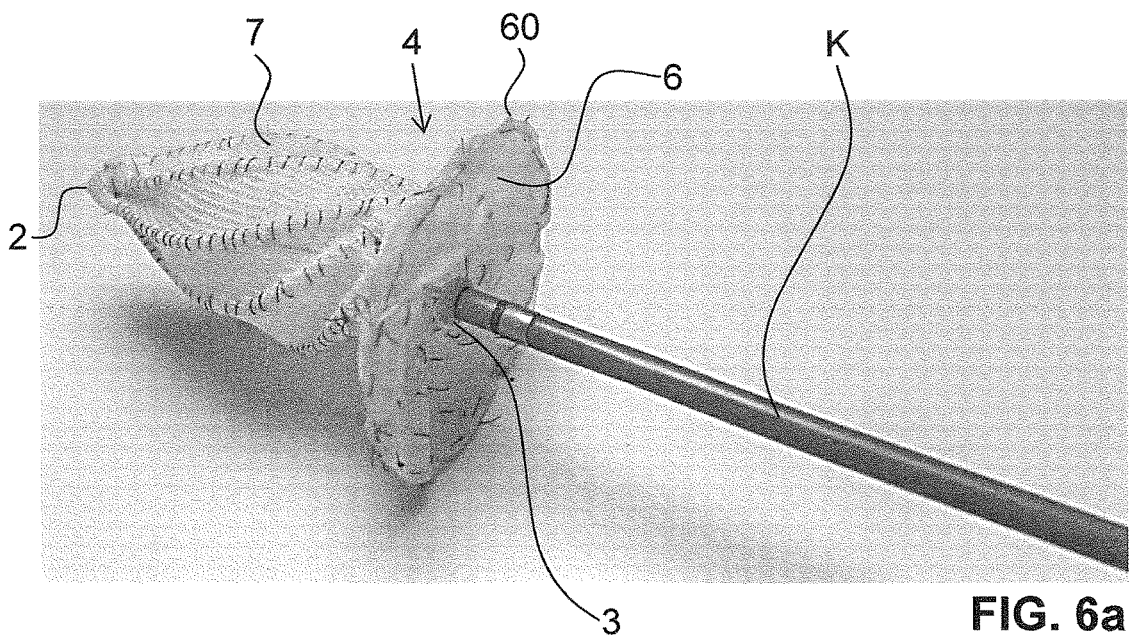
FIGS. 6a and 6b show the occluder according to FIG. 3 in a fully deployed or expanded state from a first side.
Figure 6B:
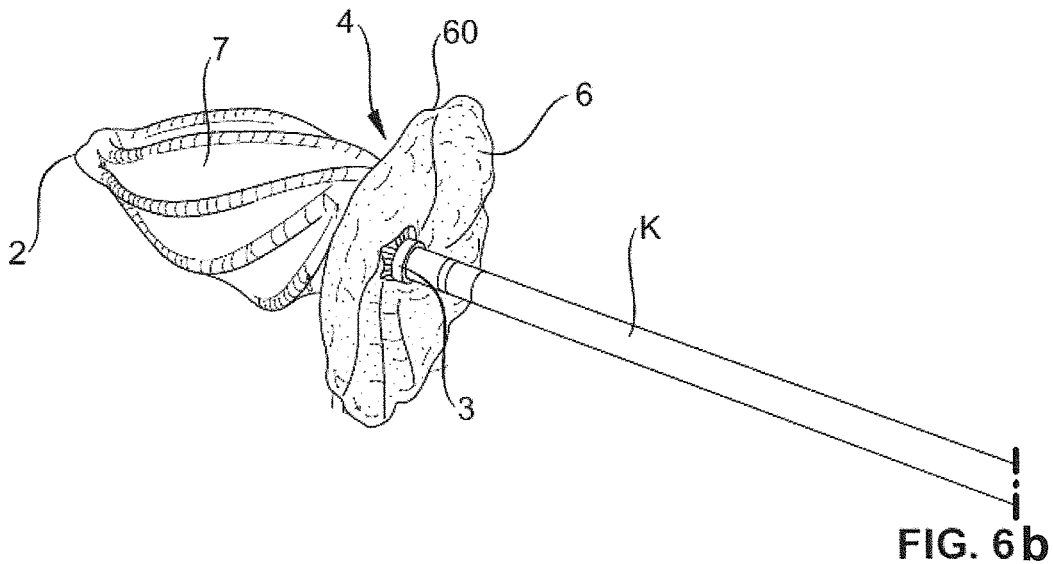

Contrary to the state of the art occluders, the first holder 2 and the second holder 3 are not brought into engagement with each other. They remain at a distance to each other, even in the fully expanded state as shown in FIGS. 6 and 7. Nevertheless, the occluder remains in this shape due to the mechanical and thermal preforming mentioned above. Preferably, the whole occluder, including all jackets, the holders and the membrane, is assembled before it is brought into an expanded shape and then heated. This expanded state is preferably the preferred final expanded state or a state similar to this final state.

Figure 8A:
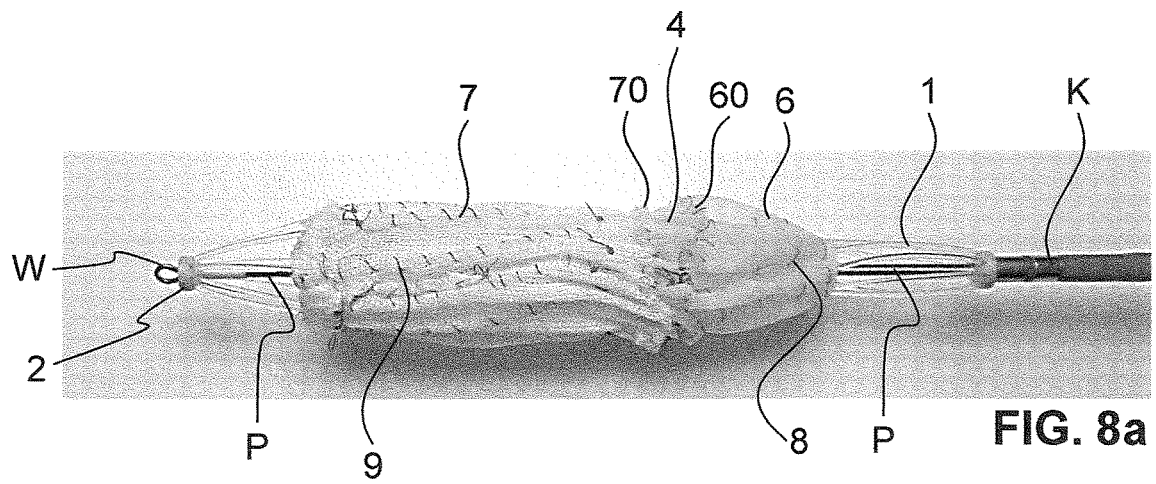
FIGS. 8a and 8b show a perspective view of an occluder according to a second embodiment of the invention in an almost completely compressed state.
Figure 8B:
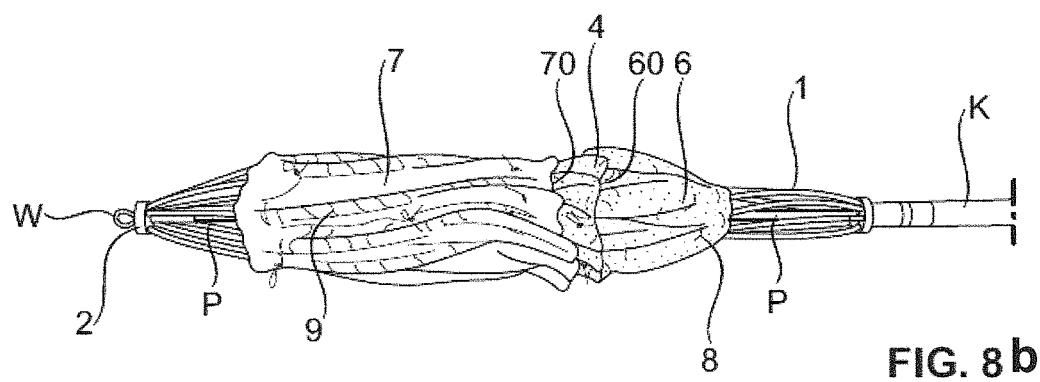
Figure 9A:
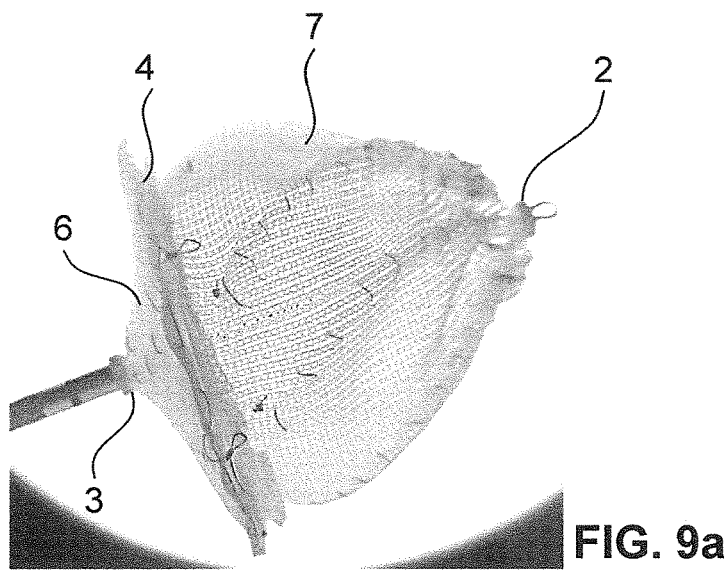
FIGS. 9a and 9b show the occluder according to FIG. 8 in a fully deployed or expanded state.
Figure 10A:
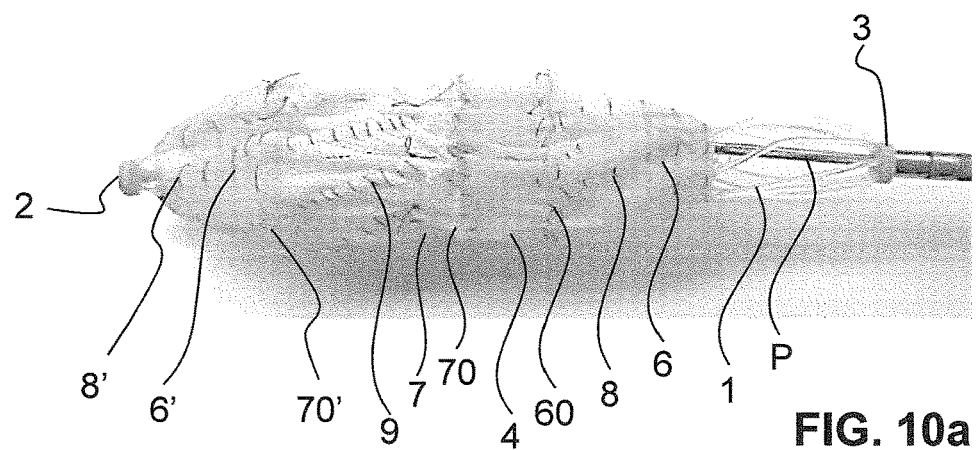
FIGS. 10a and 10b show a perspective view of an occluder according to a third embodiment of the invention in an almost completely compressed state.
Figure 11A:
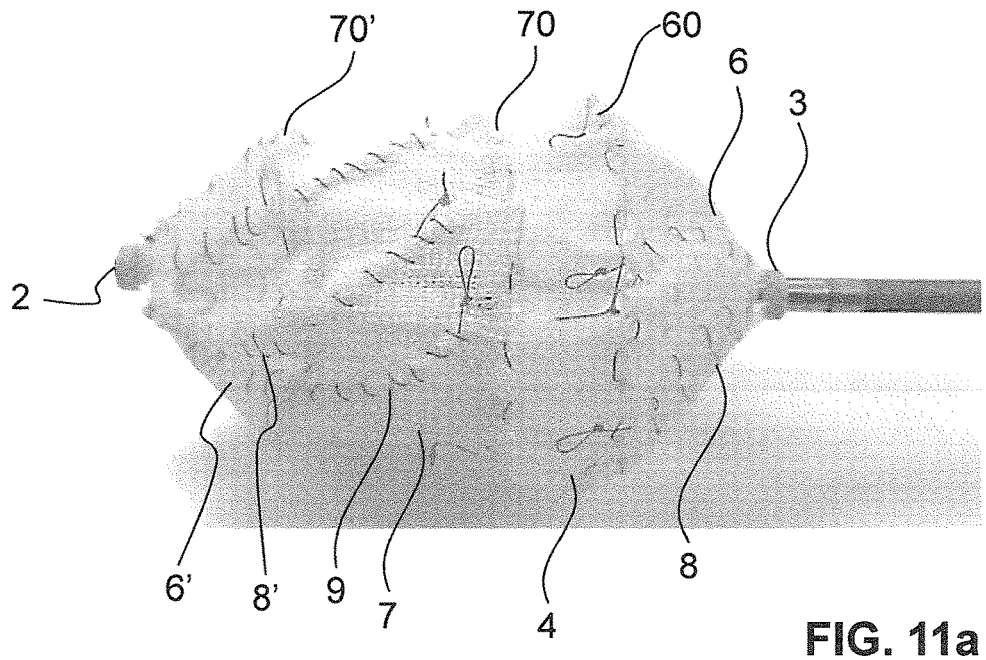
FIGS. 11a and 11b show the occluder according to FIG. 10 in a partly deployed or expanded state.
Figure 9B:
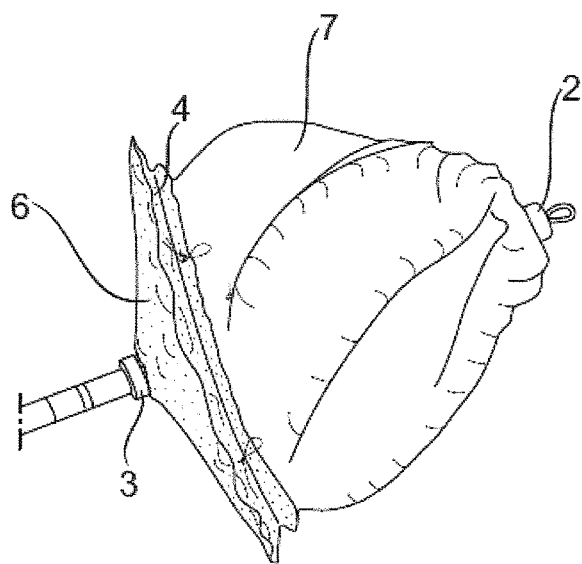
Figure 10B:
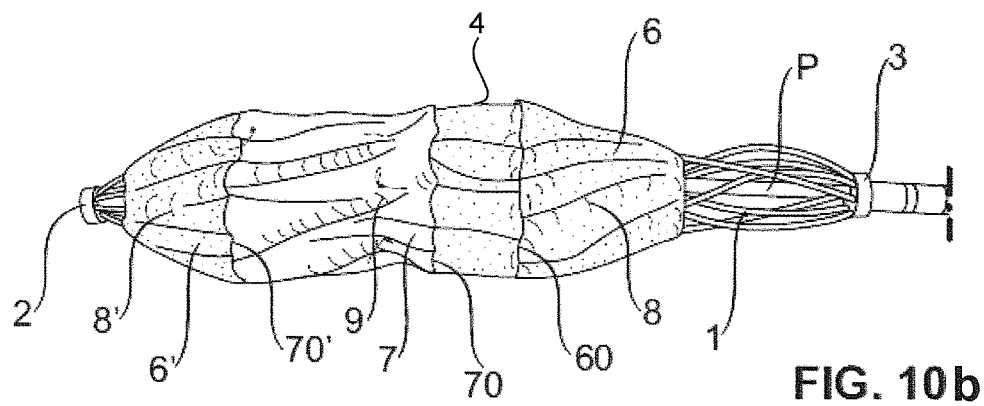
Figure 11B:
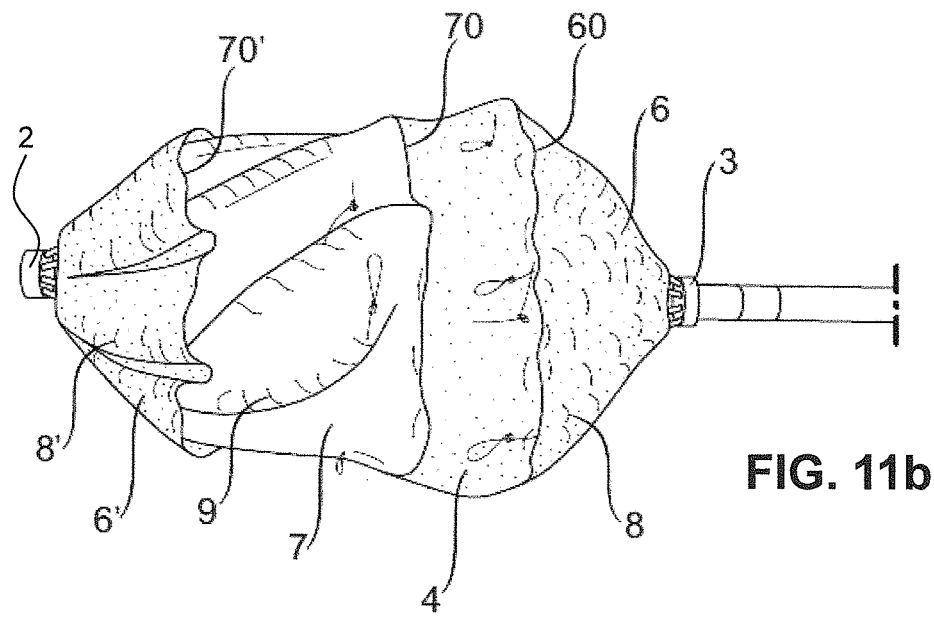

FIGS. 8 and 9 show a second embodiment of the inventive occluder. It is almost identical with the one shown in FIGS. 3 to 7. Only the second jacket 7 has a different shape and the parts of the elongate members 1 fixed to second jacket 7 are bent into a different angle than the ones of the first embodiment, as can best be seen in FIG. 9.

In FIGS. 8 and 9 a pick-up wire W is shown which protrudes from the first holder 2. This pick-up wire W is only used for placing the occluder onto a delivery mechanism. It is then pulled out of the first holder 2 and a guide wire can penetrate the through opening of the first holder 2 in order to place the occluder at a predetermined location within the human or animal body. This also applies to all other embodiments shown.

FIGS. 10 to 13 show a third embodiment. The occluder still only comprises one single membrane, the occluding membrane 4. The occluding membrane 4 is penetrated by the elongate members 1, wherein each elongate member 1 penetrates the occluding membrane 4 at a different point. These points form a co-centric circle around the central opening 40 of the occluding membrane 4, which central opening 40 can be penetrated by the control catheter P. The first jacket 6 is attached to the occluding membrane 4, both forming a common bag. The second jacket 7 is attached to the other side of the occluding membrane 4, as described in the above mentioned first and second embodiments. The materials of the occluding membrane 4 and the first and second jackets 6, 7 are preferably the same as described above. The same applies for the threads and sutures. All these features are identical with the ones of the first and second embodiment.

In this embodiment, a third jacket 6' is attached to the second jacket 7 on its distal side. This third jacket 6' preferably has the same shape as the first jacket 6. Preferably, it is round with a central opening. Preferably the first jacket 6 has a bigger diameter than the third jacket 6'. The first and third jacket 6, 6' are preferably made of the same material.

The second jacket 7 is attached to an outer circumference of the third jacket 6'. Preferably it is sewed to it. This third seam is marked with reference number 70'. The elongate members 1 are preferably sewed to the third jacket 6' as well, wherein the stitches are so loose that the third thread 8' is only a guiding means but not restricting the relative movement of the elongate members 1 relative to the third jacket 6'. The stitches of first and third threads 8, 8' correspond to the ones described in the first embodiment according to FIGS. 3 to 7. The same applies to the stitches of the second thread 9.

Figure 12A:
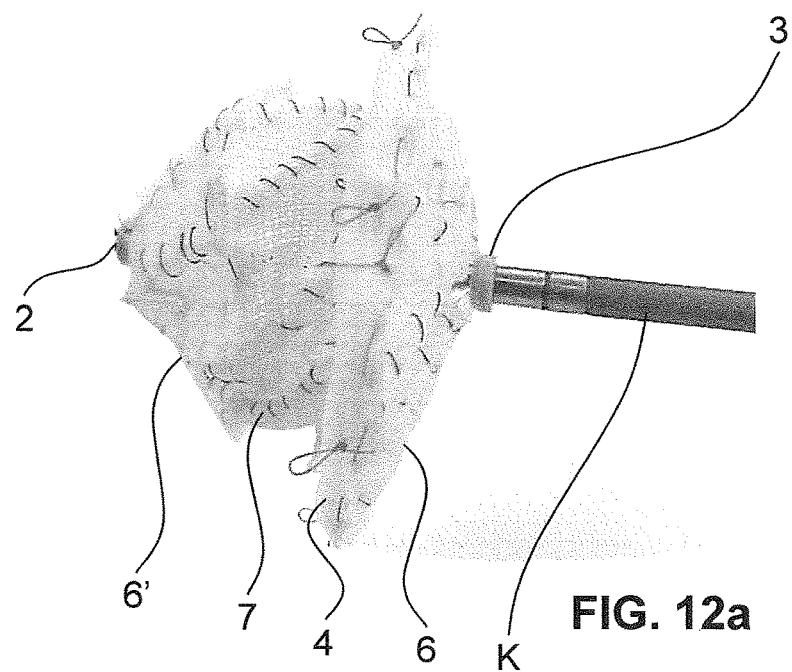
FIGS. 12a and 12b show the occluder according to FIG. 10 in a fully deployed or expanded state from a first side.
Figure 13A:
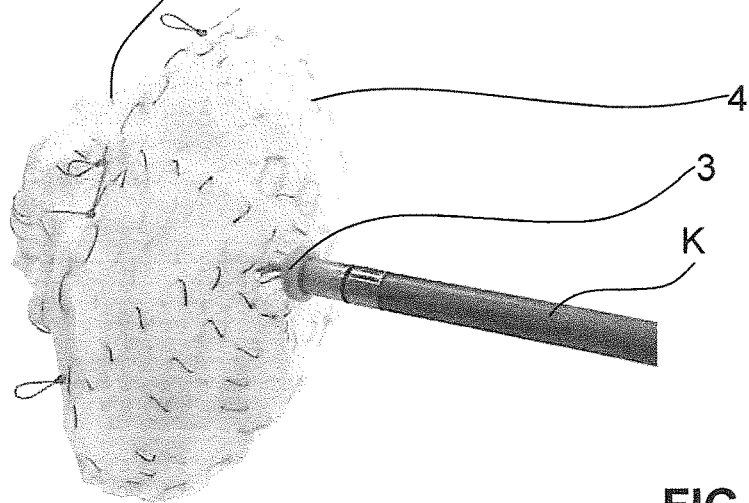
FIGS. 13a and 13b show the occluder according to FIG. 10 in a fully deployed or expanded state from a second side.
Figure 14A:
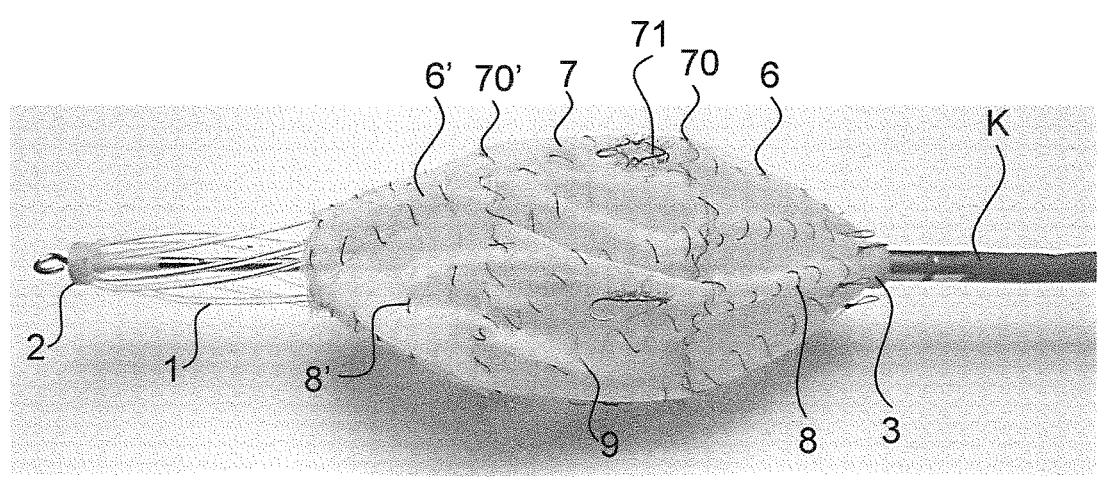
FIGS. 14a and 14b show a perspective view of an occluder according to a fourth embodiment of the invention in a compressed state.
Figure 12B:
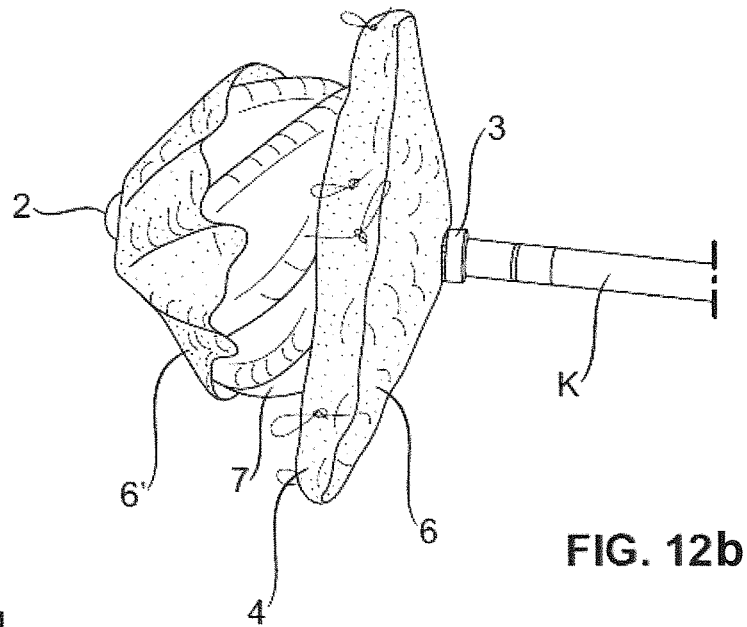
Figure 13B:
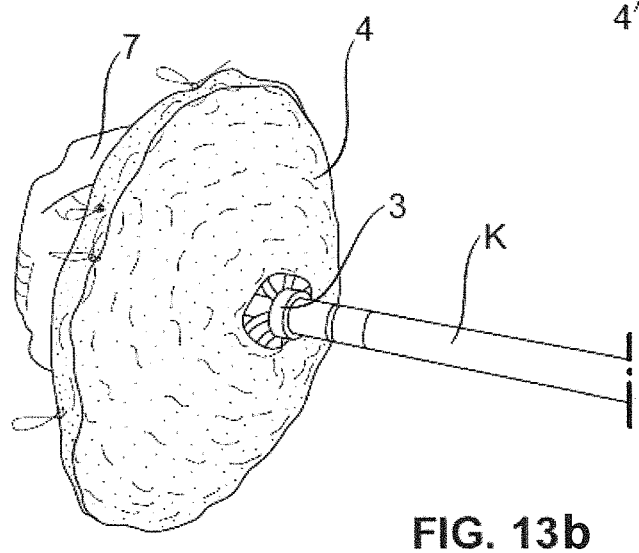
Figure 14B:
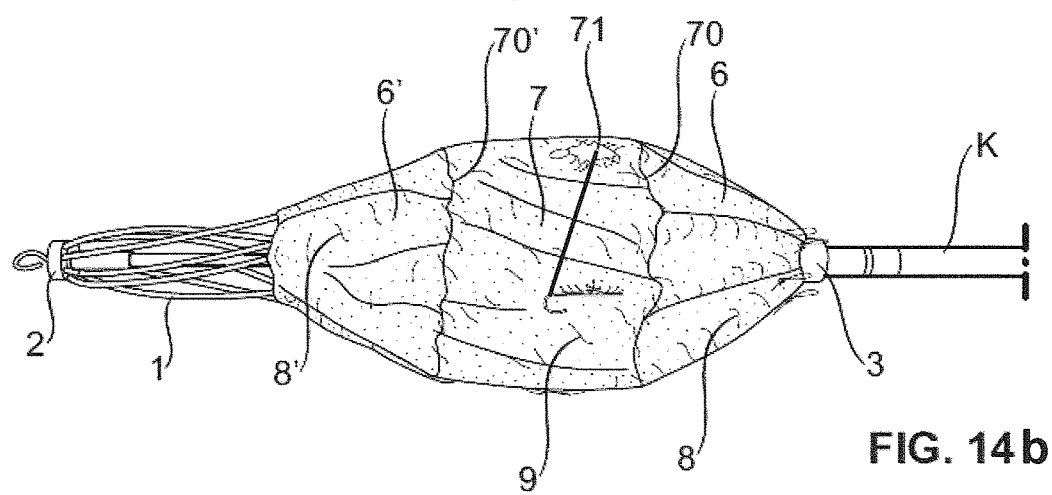
Figure 15A:
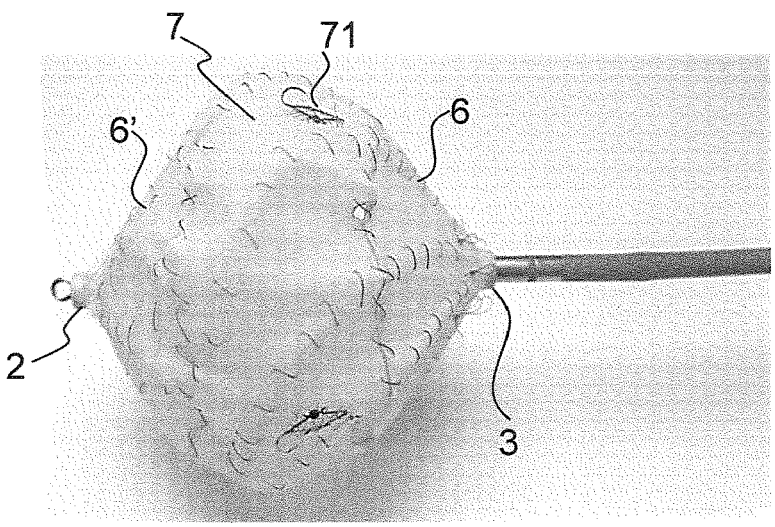
FIGS. 15a and 15b show the occluder according to FIG. 14 in a partly deployed or expanded state.
Figure 16A:
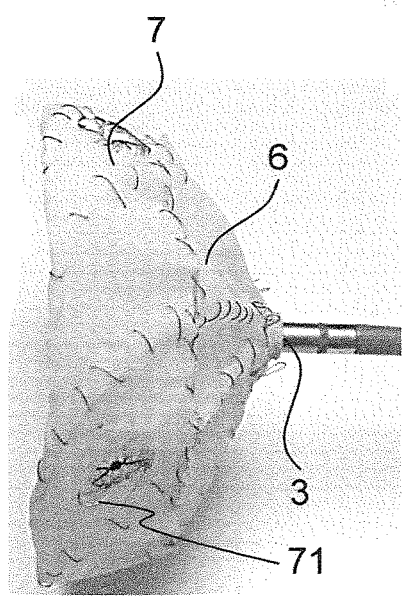
FIGS. 16a and 16b show the occluder according to FIG. 14 in a fully deployed or expanded state from a first side.

As can be seen in FIGS. 12 and 13, the occluding membrane 4 and the first jacket 6 allow the corresponding distal parts of the elongate members 1 to twist into a flower-shaped form. The third cover or jacket 6' allows the proximal parts of the elongate members 1 to bend but they are hindered in their twisting motion by the second jacket 7 in between the first and third jackets 6, 6'. The second jacket 7 has in the expanded state a shape similar to a cylinder.

In all embodiments described herein the threads or sutures of the seams 8, 8' and 9 preferably extend along a single elongate member 1 only. Preferably, for each jacket 6, 6', 7 and for each elongate member another thread or suture is used.

Figure 17A:
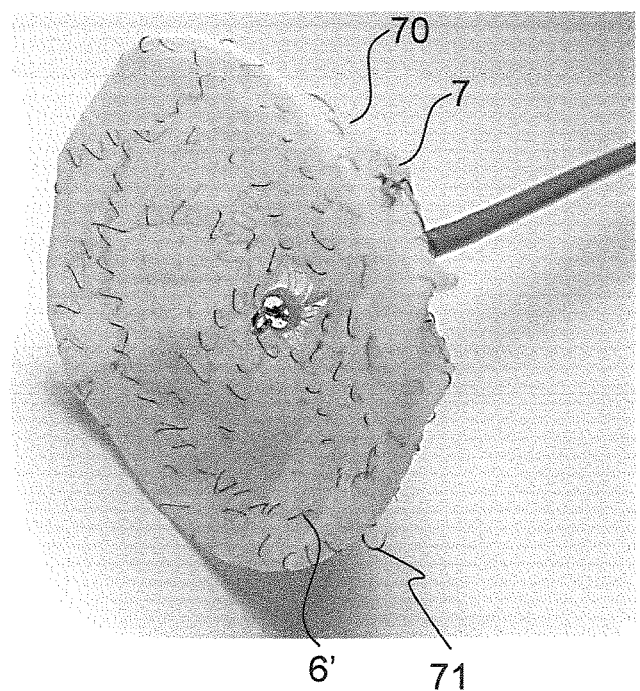
FIGS. 17a and 17b show the occluder according to FIG. 14 in a fully deployed or expanded state from a second side.
Figure 15B:
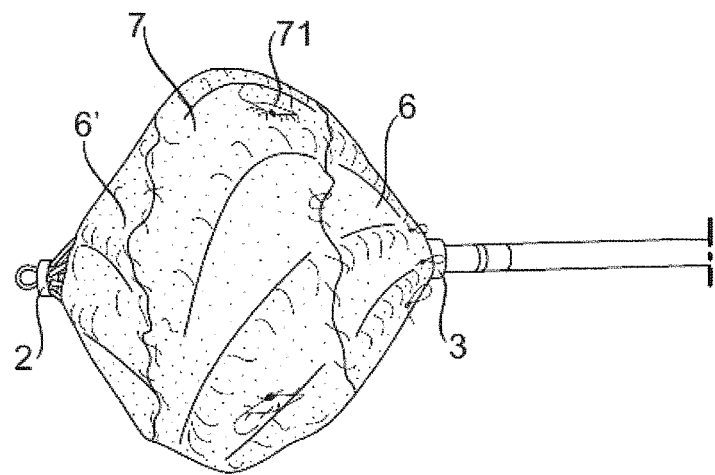
Figure 16B:
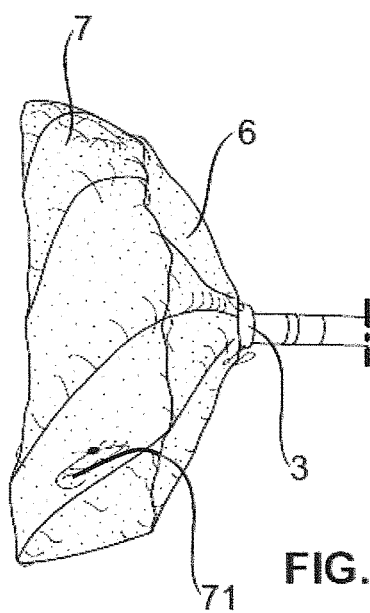
Figure 17B:
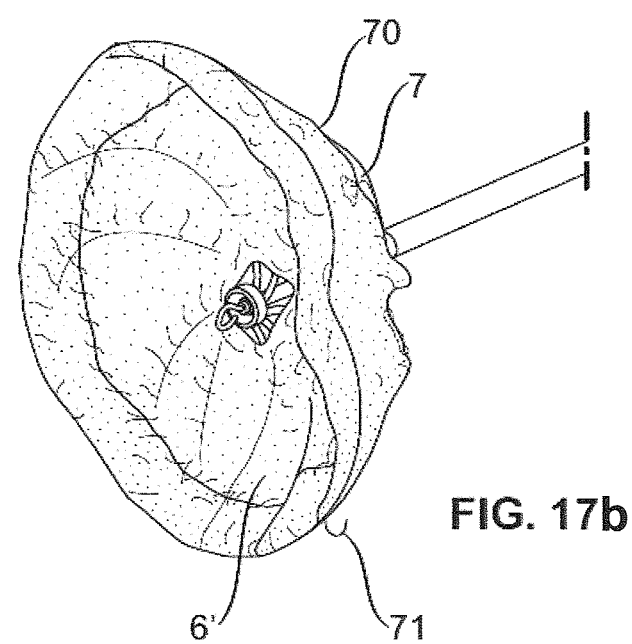

FIGS. 14 to 17 show a fourth embodiment of the inventive occluder. No membranes are present at all. The elongate members 1 are enclosed within a first, second and third jacket 6, 7, 6'. The first and third jackets 6, 6' are made of the same material as mentioned above. They have preferably a disk-shaped basic shape with a central hole for penetration of the control catheter P. They are both attached to the elongate members 1 with threads, wherein each elongate member 1 is sewed separately to the first and third jacket 6, 6'. The second jacket 7 can be made of the same material or another material as the second jacket 7 of the embodiments mentioned above. Preferably it is made of the same material as the first and third jacket 6, 6'. Preferably, each elongate member 1, extending from the first to the second holder 2, 3 as a one single piece is sewed from the first to the second holder 2, 3 along its length with the same or a continuous thread. The stitches are thereby so firm or tight, that the elongate member can still move in their longitudinal direction relative to the jackets but they are guided by the jackets into their bended position. When the first and second holders 2, 3 are brought nearer to each other, the elongate members 1 can not twist into the flower shape. They can and do however twist into a cup-like or concave shape as shown in FIG. 17. The opening of this shape is directed to the cavity of the left atrial appendage (LAA).

Hooks 71 or other retaining elements are preferably fixed to the outside of the jackets, on the distal side of the occluding part of the cover. This distal occluding part of the cover is generally the first jacket 6. The hooks 71 engage with the body tissue of the patient, holding the occluder additionally in place. The hooks 71 are preferably sewed to the material of the second jacket 7. Such hooks 71 can also be used in the other inventive embodiments described above.

In this embodiment, the first and the second holder 2, 3 are preferably brought into engagement with each other and locked into one another, for example with the well known snap lock. This shape of the expanded occluder has the advantage that also oval or elliptical shapes can be used as occluding shapes for closing the LAA aperture.

Figure 22A:
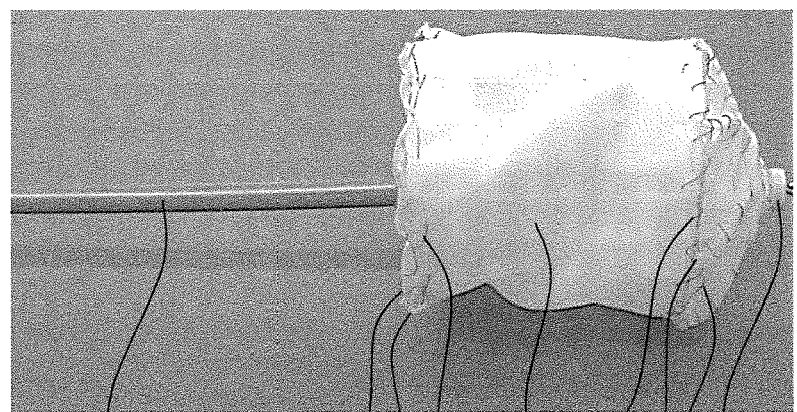
FIGS. 22a and 22b show another embodiment of an inventive occluder in a first view in its expanded state.
Figure 23A:
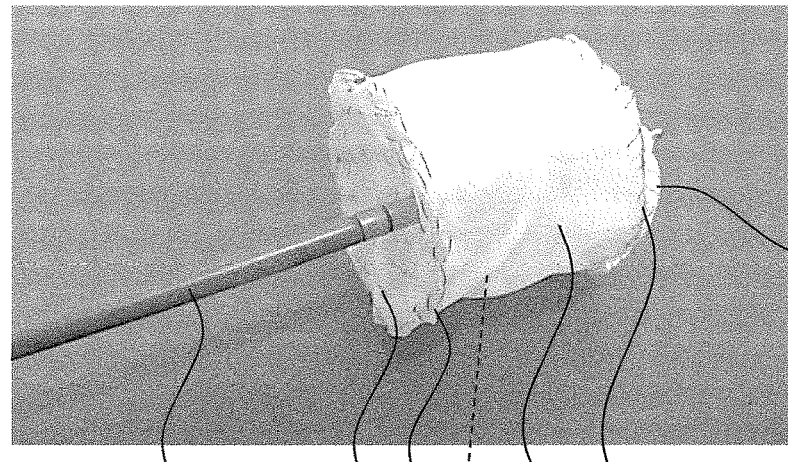
FIGS. 23a and 23b show the occluder of FIG. 22 in a second view.
Figure 24A:
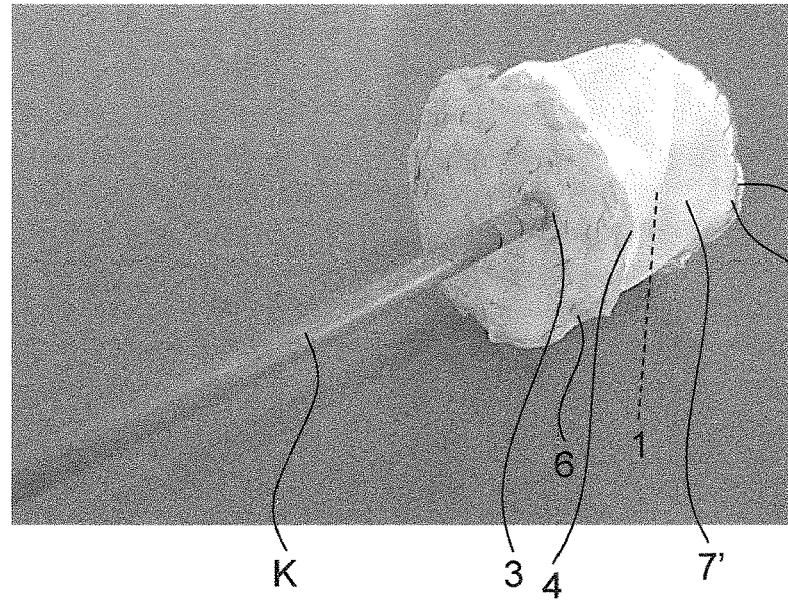
FIGS. 24a and 24b show the occluder of FIG. 22 in a third view.
Figure 22B:
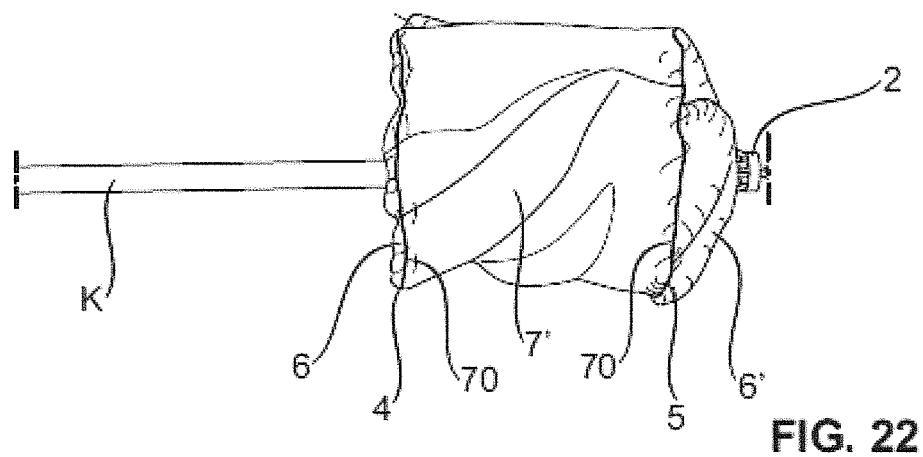
Figure 23B:
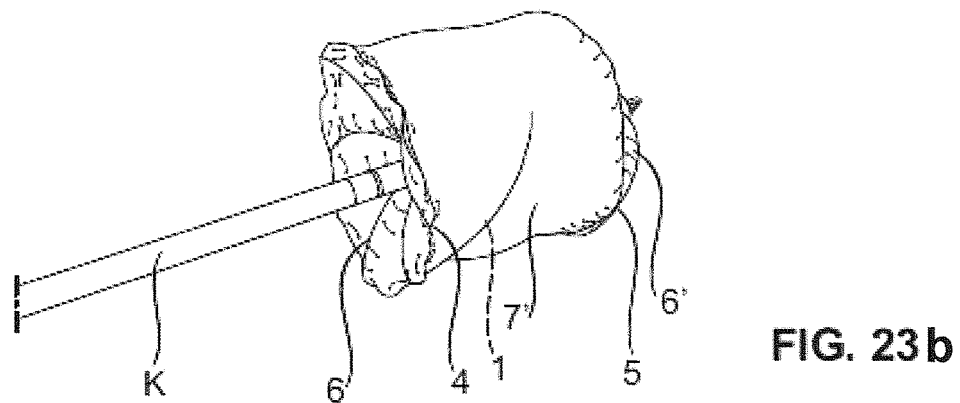
Figure 24B:
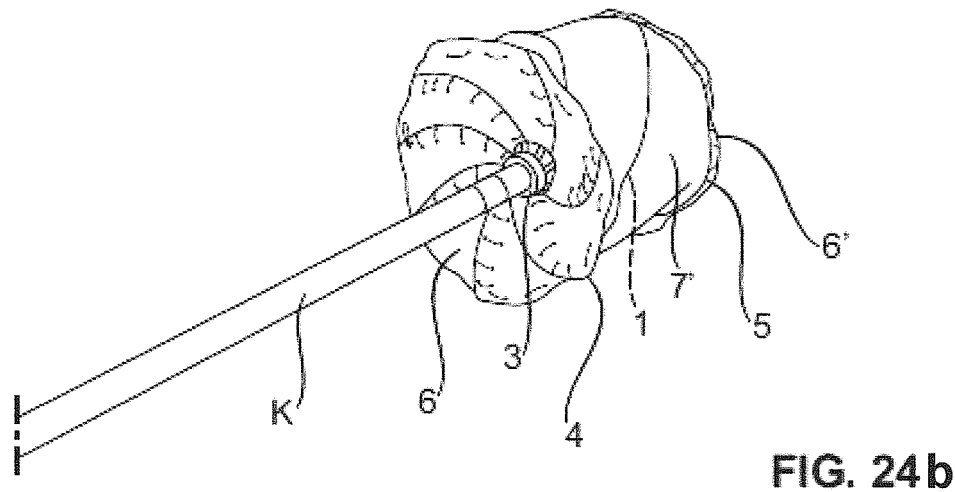

FIGS. 22 to 24 show another inventive occluder. The same reference numbers are used for the same elements. This occluder also comprises the elongate members 1 hold in or fixed to first and second holders 2, 3. The expanding structure is therefore the same as mentioned above. Both holders 2, 3 can again be moved and controlled independently from each other. The occluder comprises a first and a third jacket 6, 6' attached to a first and a second membrane 4, 5. The elongate members 1 are sewed or otherwise attached to the first and second jackets 6, 6' as mentioned above; i.e. by still allowing to elongate members to move relative to the jackets 6, 6'. The occluder corresponds so far to the embodiment according to FIG. 2. According to the invention, a middle second jacket 7' is arranged between the first and second membrane 4, 5 and fixed to them. Preferably it is sewed to them. Contrary to the embodiments mentioned above, the elongate members are not fixed to this second jacket 7' but are only enveloped by it. However, the shape, especially the diameter, of the second jacket 7' is preferably such that the elongate members 1 can or does not take their stent-like shape between the two membranes 4, 5 as shown in FIG. 1. The occluder as shown in the FIGS. 22 to 24 is already in its fully and final expanded state. It remains in this state, even without the holders being locked into each other, since it is mechanically and thermally preformed as well. This preform is made as described above, preferably when the occluder is fully assembled.

FIGS. 25 to 31 show a preferred embodiment of a holder system and of an occluder using this holder system. The occluder can be an occluder incorporating the inventive ideas as described above, namely one of the embodiments described above. However, the inventive holder system can also be used in another kind of occluder, such as the ones mentioned in the state of the art. For example, it can be used in occluders as described in the state of the art, such as in U.S. Pat. No. 6,488,706, US 2003/0149463, WO 2005/074813 and WO 2012/156415.

The occluder system comprises the distal first holder 2 and the proximal second holder 3 as can be seen in FIG. 25. The first holder 2 comprises a first holder head 20 and a stem 24. A through opening 22 extends through the first holder head 20 and the stem 24 and connects both ends of the first holder 2, wherein the through opening 22 comprises at its distal end an inner thread 23.

Figure 28:
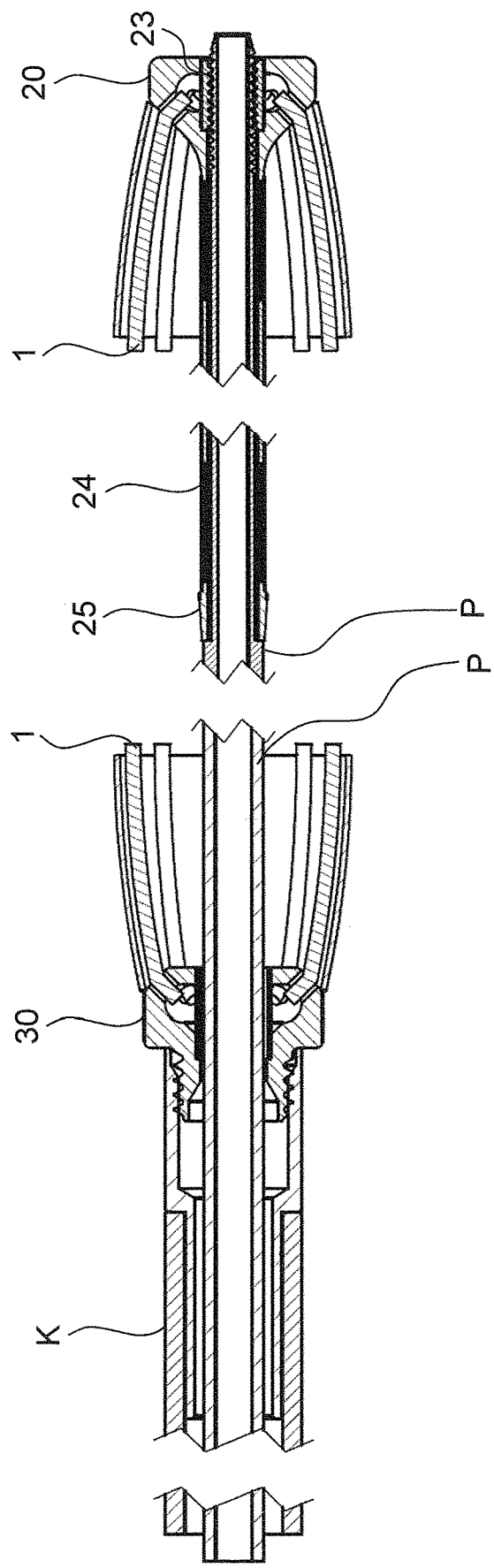
FIG. 28 shows an occluder with a pair of holders according to FIG. 25 in a longitudinal sectional view in a compressed state and with a delivery catheter and control catheter.

As can be seen in FIG. 27, there are fixation openings 21 radially distributed around the first holder head 20. In these fixation openings 21 the elongate members 1 are hold, as can be seen in FIG. 28.

The proximal end region of the stem 24 is formed like a surrounding retaining nose 25.

The stem 24 can be made of one single part. It can be made of a stiff or a flexible material. In the embodiment shown, the stem 24 consists of several parts fixedly connected to each other, wherein the middle part is preferably made of a flexible material. It is for example made of a cable tube.

As can be seen in FIG. 26, the second proximal holder 3 comprises a second holder head 30 with fixation openings 31 for the elongate members 1 as well. It also comprises a through opening 32 connecting his ends. Instead of an inner thread, an outer thread 33 is present. The through opening 32 changes its inner diameter, wherein a circumferential retaining edge 34 is formed.

FIGS. 28 to 31 show how this occluder is brought into its expanded shape. In FIG. 28, the occluder is compressed. The delivery catheter K is coupled to the outer thread 33 of the proximal second holder 3. The control catheter P is coupled to the inner thread 23 of the distal first holder 2, wherein this control catheter P penetrates the stem 24.

Figure 29:
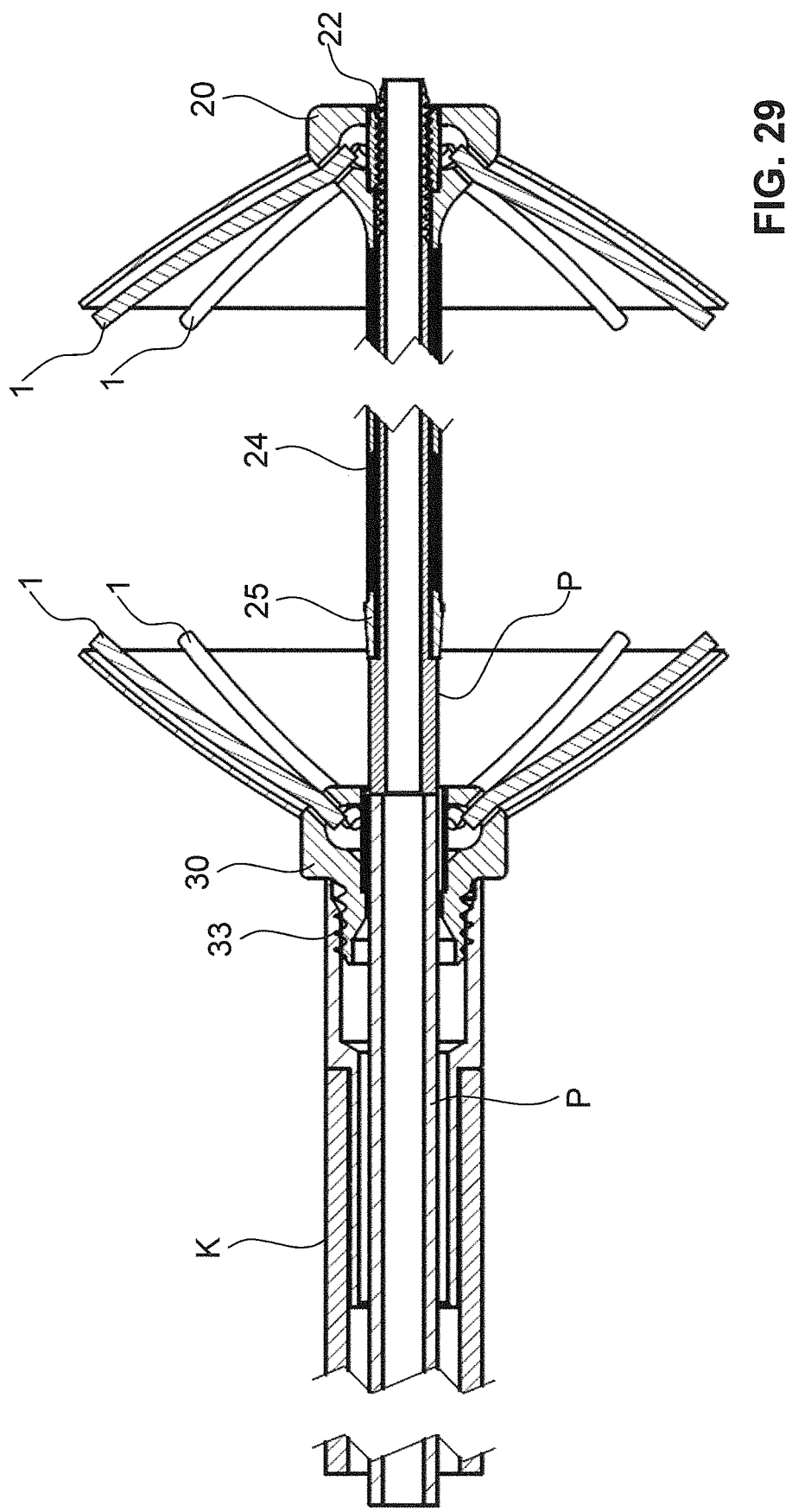
FIG. 29 shows the occluder of FIG. 28 in a partially deployed state.
Figure 30:
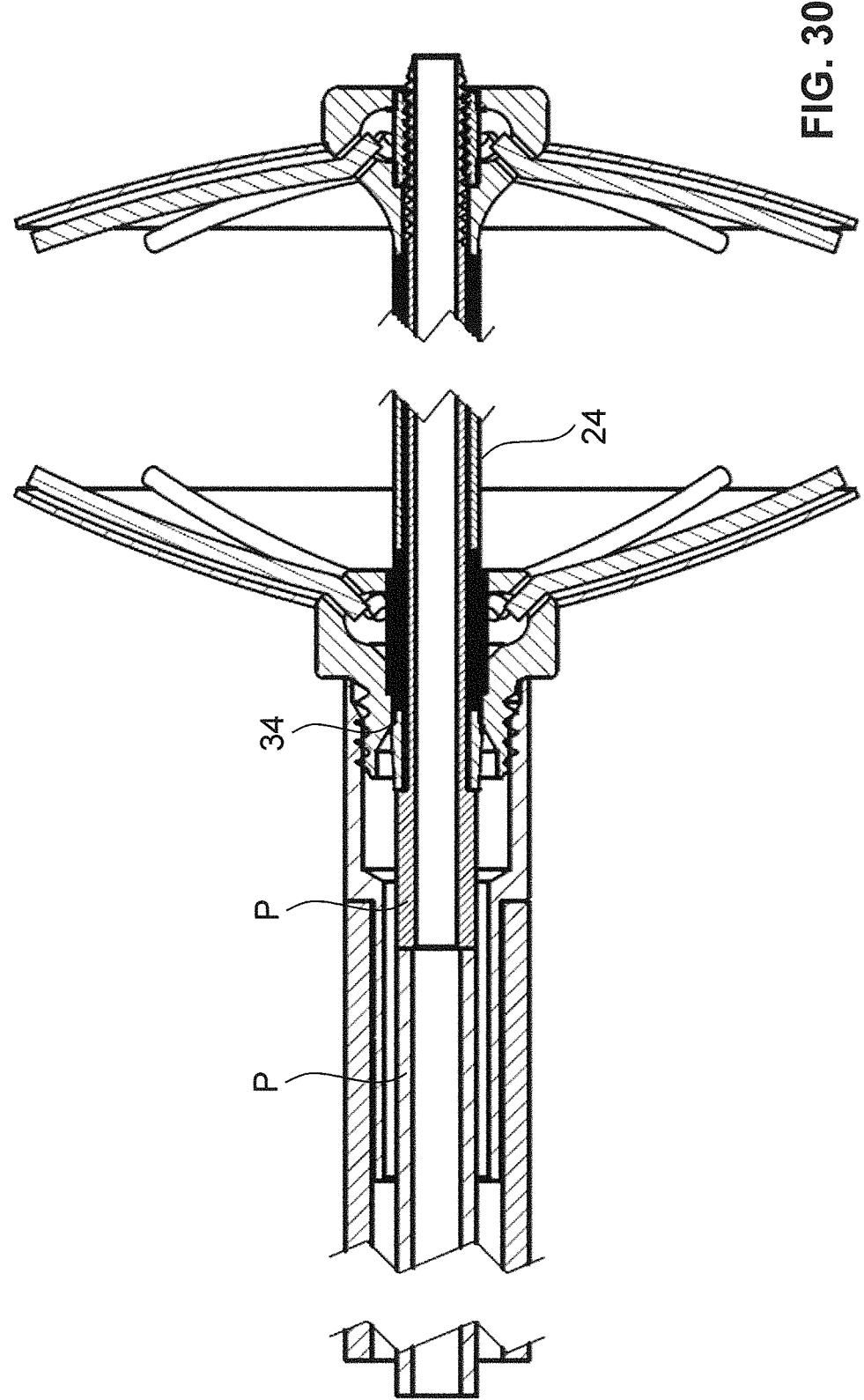
FIG. 30 shows the occluder of FIG. 28 in a fully deployed state.
Figure 31:
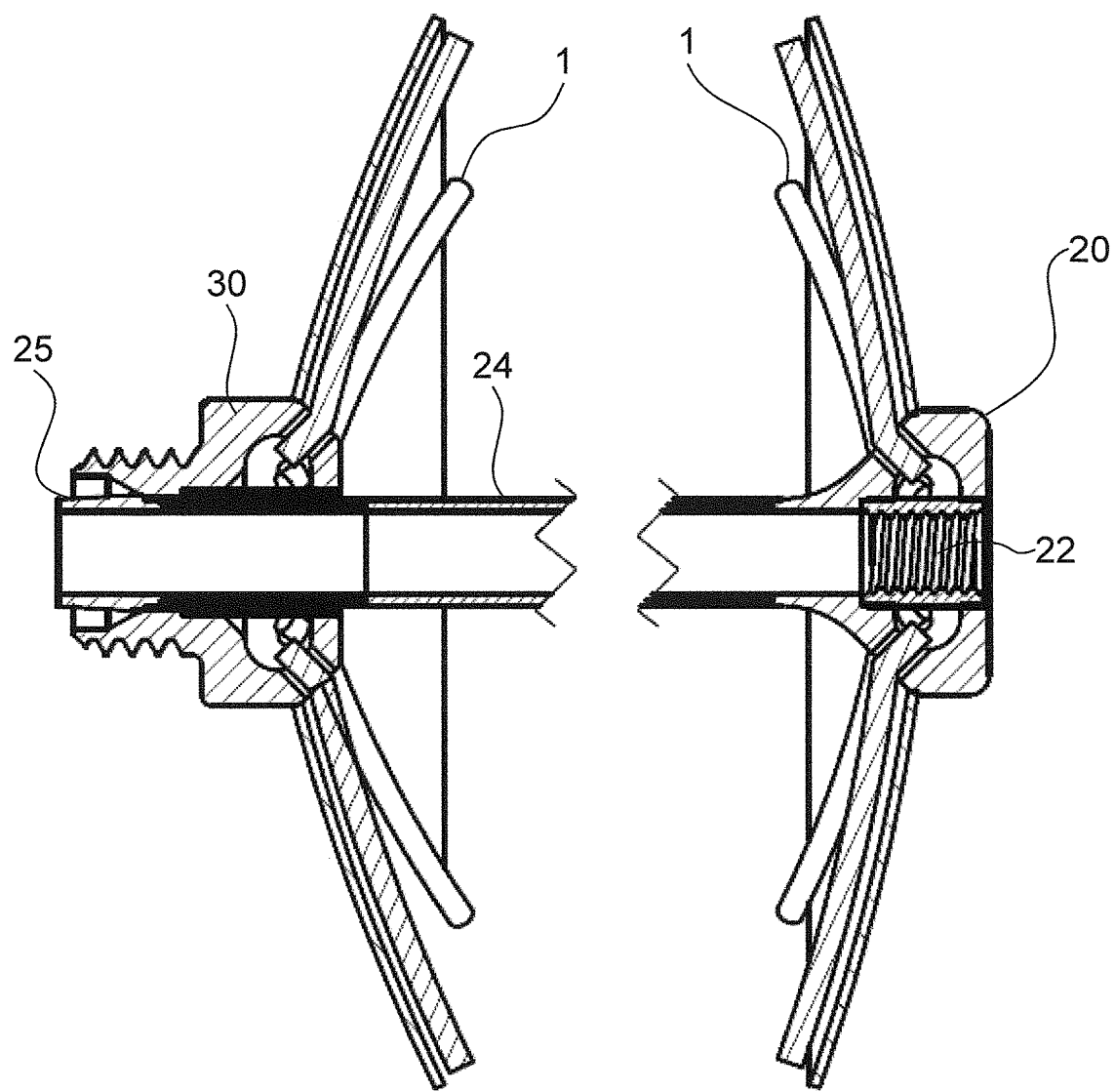
FIG. 31 shows the occluder of FIG. 30 without delivery and control catheter.

The control catheter P can be made of one single piece or it can, as can best be seen in FIG. 29, consists of several pieces. It can especially comprise a head with an outer thread engaging the inner thread 23 of the first holder 2 and a circumferential abutting edge which abuts the proximal end of the circumferential retaining nose 25. This abutting edge prevents the control catheter P to be screwed further into the first holder head 20.

As can be seen in FIG. 29, the two holders 2, 3 are approximated to each other by pushing the delivery catheter K forward and/or by pulling the control catheter P backwards. This accomplished until the retaining nose 25 of the first holder 2 clicks or snaps into the retaining edge 34 of the second holder 3.

Depending on the consistence of the surface of the stem 24 and the inner side of the second holder 3, the stem 24 remains movable relative to the inner surface of the first holder 2 along the longitudinal axis of the holder system. This movement is however restricted in one direction by the retaining action of the nose 25 and edge 34. This means that in some embodiments, the occluder can still be brought in a more expanded state but can not be brought back into the compressed state unless the connection between stem 24 and edge 34 of the second holder 3 is released.

The stem 24 is a guide for the opening action of the occluder when the occluder is brought into its expanded state, since the holder heads are guided along the longitudinal axis defined by the stem 24.

The length of the stem 24 defines the maximum distance of the two holders 2, 3. This length and therefore this distance can be chosen such, that the occluder is hold in a loaded or tensioned state; for example when the elongate members are thereby forced to bend such that they stretch the enveloping jacket. This increases the radial forces acting on the occluder.

The occluder according to the invention uses the well known expanding structure which can be easily handled whereby the movement of the elongate members is restricted by at least one of the jackets which envelop the elongate members. The elongate members and other parts of the occluder can be made of bioresorbable material.

The invention claimed is:

1. An occluder for occluding a passage in a body, especially in a left atrial appendage, wherein the occluder comprises elongate members, each elongate member having a length with a first end and a second end, the first end being held in or attached to a first holder and the second end being held in or attached to a second holder, wherein the elongate members extend independently from each other between the first and the second holder and wherein the elongate members are collectively enveloped at least over a part of their length by a first jacket and a second jacket, wherein at least the second jacket restricts a bending motion of the elongate members when their first ends are approximated to their second ends by moving the two holders relatively to each other and wherein a portion of the elongate members restricted in its bending motion is surrounded by the second jacket and wherein a portion of the elongate members arranged in the first jacket is not restricted in its bending motion or less restricted than the portion of the elongate members arranged in the second jacket.

2. The occluder of claim 1 wherein all elongate members are completely enveloped by the first jacket and the second jacket in an expanded final state of the occluder.

3. The occluder of claim 1 wherein at least a portion of the elongate members are attached to the first jacket and the second jacket.

4. The occluder of claim 3 wherein all of the elongate members are attached to the first jacket and the second jacket.

5. The occluder of claim 3 wherein the elongate members are sewed to the first jacket and the second jacketor wherein the first jacket and the second jacket comprise pockets for holding elongate members, wherein each pocket holds one single elongate member only.

6. The occluder of claim 1 wherein the elongate members are restricted in their bending motion for only a portion of their length.

7. The occluder of claim 1 wherein the occluder further comprises an occluding membrane penetrated by the elongate members, wherein the occluding membrane is deployable by a twisting motion of the elongate members when the first holder and the second holder are moved relative to each other.

8. The occluder of claim 7 wherein the occluding membrane is fixed to the first jacket and the second jacket is fixed to the occluding membrane, wherein the bending motion of a portion of the elongate members enveloped by the second jacket is restricted.

9. The occluder of claim 8 wherein the first jacket allows a twisting motion of the portions of the elongate members enveloped by the first jacket.

10. The occluder of claim 7 wherein the occluding membrane is fixed to the first jacket and the second jacket is fixed to the occluding membrane, wherein the portions of the elongate members arranged within the first jacket are fixed to the first jacket allowing movement of the elongate members relative to the first jacket and wherein the portions of the elongate members arranged within the second jacket are fixed to the second jacket allowing less or no movement relative to the second jacket, so that the bending motion of these portions of the elongate members is restricted by the second jacket.

11. The occluder of claim 1 wherein the occluder further comprises a third jacket wherein the third jacket is fixed to the second jacket on a side opposite to an occluding membrane and wherein the third jacket allows more motion of the portion of the elongate members enveloped by this third jacket.

12. The occluder of claim 1 wherein the occluder comprises the first jacket, the second jacket fixed to the first jacket and a third jacket fixed to the second jacket, the first, second and third jackets forming a common bag and the elongate members being fixed along their length to the first jacket, second jacket and third jacket, and wherein the second jacket restricts the bending movement of the elongate members more than the first jacket and third jacket, wherein the elongate members are twisting with their enveloping first jacket, second jacket and third jacket into a cup-shaped form when the two holders are brought together.

13. The occluder of claim 1 wherein at least one retaining element is arranged on an outside of the first and the second jacket.

14. The occluder of claim 1 wherein the first holder comprises a through hole with a first retaining element and the second holder comprises a stem with a second retaining element, wherein the first and the second retaining element are brought into engagement with each other in an expanded final state of the occluder.

15. The occluder of claim 14 wherein the first and the second holder are able to move along the stem relative to each other in the expanded final state wherein the first and the second retaining element together form an abutment of this movement.

16. A method to produce an occluder according to one of claims 1 to 15 wherein the method comprises the steps of
attaching elongate members of the occluder to at a first jacket and a second jacket, wherein each elongate member is attached separately,
restricting a second portion of the elongate members in its bending motion by surrounding the first portion of the elongate members with the second jacket and
not restricting or less restricting a first portion of the elongate members in its bending motion by surrounding the first portion of the elongate members with the first jacket,
bringing the occluder with the attached elongate members into an expanded shape by approximating the two holders connected with the elongate members to each other,
holding the occluder in this expanded shape and
heating the occluder to mechanically and thermally preform the occluder.

17. An occluder for occluding a passage in a body, especially in a left atrial appendage, wherein the occluder comprises elongate members, each elongate member having a length with a first end and a second end, the first end being held in or attached to a first holder and the second end being held in or attached to a second holder, wherein the elongate members extend independently from each other between the first and the second holder, wherein the elongate members are collectively enveloped over a first part of their length by a first jacket and wherein the elongate members are collectively enveloped over a second part of their length by a second jacket,
wherein at least one of the first jacket and the second jacket restricts a bending motion of the elongate members when their first ends are approximated to their second ends by moving the two holders relative to each other,
wherein the occluder further comprises a first occluding membrane and a second occluding membrane, the first and second occluding membranes being penetrated by the elongate members, wherein the first and second occluding membranes are deployable by a twisting motion of the elongate members when the first holder and the second holder are moved relative to each other, wherein the first and second occluding membranes are fixed to the first jacket and the second jacket, wherein the occluder comprises a middle jacket arranged between the first and the second occluding membrane and wherein the elongate members extend within this middle jacket non-attached to the middle jacket, and wherein the portion of the elongate members restricted in its bending motion is surrounded by the second jacket and wherein a portion of the elongate members arranged in the first jacket is not restricted in its bending motion or less restricted than the portion of the elongate members arranged in the second jacket.

* * * * *